United States Patent [19]
Shapiro et al.

[11] Patent Number: 5,477,468
[45] Date of Patent: Dec. 19, 1995

[54] CONCENTRATION ANALYZER

[75] Inventors: Philip Shapiro, Frederick, Md.; Julian D. Warhurst, Ashland, Mass.

[73] Assignee: Project CD, Frederick, Md.

[21] Appl. No.: 181,060

[22] Filed: Jan. 14, 1994

[51] Int. Cl.[6] ................................................. G01N 27/22
[52] U.S. Cl. ...................... 364/499; 364/497; 73/61.61; 436/53; 128/632; 128/692
[58] Field of Search ................................ 364/496, 497, 364/499; 128/632, 635, 692; 436/52, 53; 73/61.61

[56] References Cited

U.S. PATENT DOCUMENTS

| | | | |
|---|---|---|---|
| 3,919,051 | 11/1975 | Koch et al. | 195/103.5 R |
| 3,930,957 | 1/1976 | Cummings et al. | 195/103.5 R |
| 4,009,998 | 3/1977 | Benningfield, Jr. | 23/230 R |
| 4,585,007 | 4/1986 | Uchigaki et al. | 128/632 |
| 4,736,748 | 4/1988 | Nakamura et al. | 128/632 |
| 4,908,676 | 3/1990 | Bedell et al. | 356/72 |
| 4,958,295 | 9/1990 | Davidson et al. | 364/497 |
| 5,080,866 | 1/1992 | Petty et al. | 436/53 |
| 5,137,831 | 8/1992 | Gusteser | 436/52 |
| 5,149,661 | 9/1992 | Gjerde et al. | 436/178 |
| 5,204,264 | 4/1993 | Kaminer | 436/8 |
| 5,333,609 | 8/1994 | Bedingham et al. | 128/632 |
| 5,335,658 | 8/1994 | Bedingham et al. | 128/632 |

*Primary Examiner*—Emanuel T. Voeltz
*Assistant Examiner*—Kyle J. Choi
*Attorney, Agent, or Firm*—Arent Fox Kintner Plotkin & Kahn

[57] ABSTRACT

The concentration analyzer of the present invention is used to determine the cross-sectional concentration at multiple locations within a fluid line, such as an artery or vein, of dissolved substances within a moving fluid flowing through the vein which fluid consists of a first solution of unknown concentration.

3 Claims, 5 Drawing Sheets

CONCENTRATION ANALYZER

BACKGROUND OF THE INVENTION

The present invention relates to a concentration analyzer comprised of an electronic computer implemented device which measures and displays the cross-sectional distribution of dissolved substances in a moving fluid stream. Specifically, the concentration analyzer of the present invention can determine the instantaneous concentration at multiple locations (called regions) in the cross section of an arterial or venous line while the fluid flow continues moving.

Traditionally, it was almost impossible to obtain accurate data about fluid concentrations within a fluid stream without using an invasive technique. Additionally, prior methods of analyzing fluid concentration could not do so in an instantaneous fashion.

The present invention is useful for measuring the delivery and even dispersion of anticoagulant agents, radioopaque contrast agents, and various chemical agents and also has numerous regional chemotherapeutic applications and has applications in non-medical areas as well.

SUMMARY OF THE INVENTION

It is therefore an object of the present invention to provide a concentration analyzer which can measure the concentration at multiple locations in the cross section of a fluid line.

It is an additional object of the present invention to provide a concentration analyzer which can obtain instantaneous measurements of concentrations within a fluid line while the fluid flow continues moving.

Additional objects and advantages of the invention will be set forth in part in the description which follows, and in part will be obvious from the description, or may be learned by practice of the invention. The objects and advantages of the invention may be realized and obtained by means of the instrumentalities and combinations particularly pointed out in the appended claims.

To achieve the objects and in accordance with the purposes of the invention, as embodied and broadly described herein, the concentration analyzer for determining the cross-sectional concentration at multiple locations within a moving fluid stream of dissolved substances consisting of a first solution of unknown concentration, comprises injection means, for introducing a second solution of known concentration of dissolved substances into the fluid flow; sensor means, for measuring the conductivity of the first solution and second solution mixture; storage means, for storing the measured conductivity at a plurality of time intervals as the moving fluid stream continues moving; and computing means, for converting the measured conductivity into a concentration value and for computing the concentration of the first solution based upon the known concentration of the second solution.

The accompanying drawings, which are incorporated in and constitute a part of this specification, illustrate an embodiment of the invention and, together with the description, serve to explain the principles of the invention.

Figure 1:
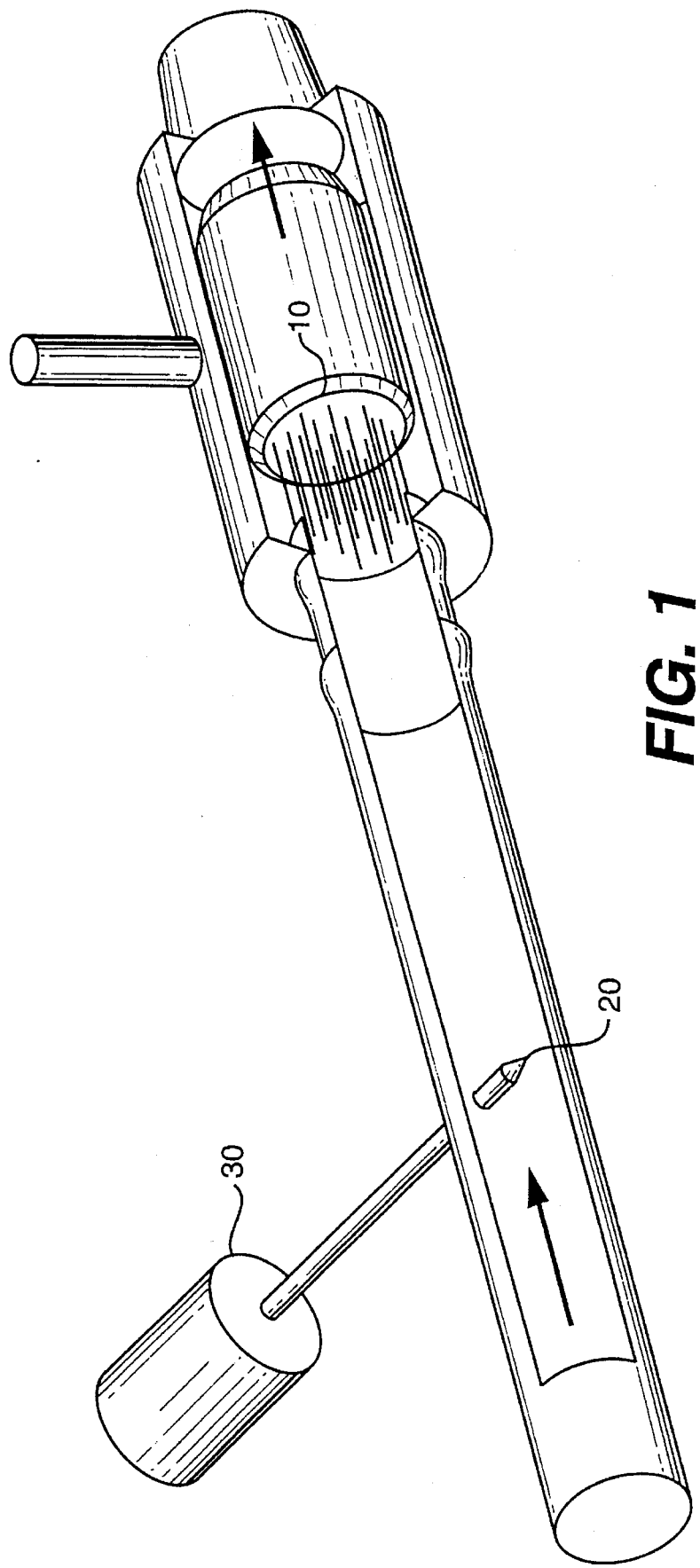
FIG. 1 is a diagram illustrating the placement of the sensor means of the concentration analyzer within the moving fluid stream in accordance with the preferred embodiment of the present invention.

EXHIBIT 1 is the MAIN PROGRAM code;

EXHIBIT 2 is the "CONDUCT.CPP" subroutine which downloads configuration information and concentration measurements;

EXHIBIT 3 is the "CREATE.CPP" subroutine which creates the configuration files used by "CONDUCT.CPP";

EXHIBIT 4 is the "SCREEN.CPP" subroutine which provides the screen graphics used by "CONDUCT.CPP"; and EXHIBIT 5 is the "SER.CPP" subroutine which transmits data to "CONDUCT.CPP."

DESCRIPTION OF THE PREFERRED EMBODIMENT

Reference will now be made in detail to the present preferred embodiment of the invention, an example of which is illustrated in the accompanying drawings in which like reference characters refer to corresponding elements.

The concentration analyzer of the present invention is used to determine the cross-sectional distribution of dissolved substances in an arterial or venous line.

It is a general principle that normal arterial flow has an evenly mixed electrolyte balance throughout the cross section of the artery. When electrodes are inserted into the fluid stream, the fluid conductivity can be measured in each region of the artery and, if the electrolytes are evenly mixed, the conductivity of each region will be identical. In accordance with the present invention, if a test solution with a different electrolyte balance is added into the arterial flow, there will be a change in the localized electrolyte levels in each region of the cross section. These changes can be measured as a change in conductivity, and the actual fluid concentrations computed.

A typical application of the present invention is illustrated in FIG. 1. A sensor 10, consisting of an electrode cluster 10(a)–(c) is inserted downstream of an infusion sight 20 into the artery or vein wherein the venous fluid is flowing. The fluid flow in the artery consists of a first, existing electrolyte solution. At the infusion sight 20, a second electrolyte solution is introduced through an injection means 30 and is mixed with the first, existing electrolyte solution. Localized differences in the electrolyte levels of individual regions of the artery will be detected as conductivity changes at the sensor 10 as the first solution-second solution mixture flows past the electrode cluster 10(a)–(c).

Figure 2:
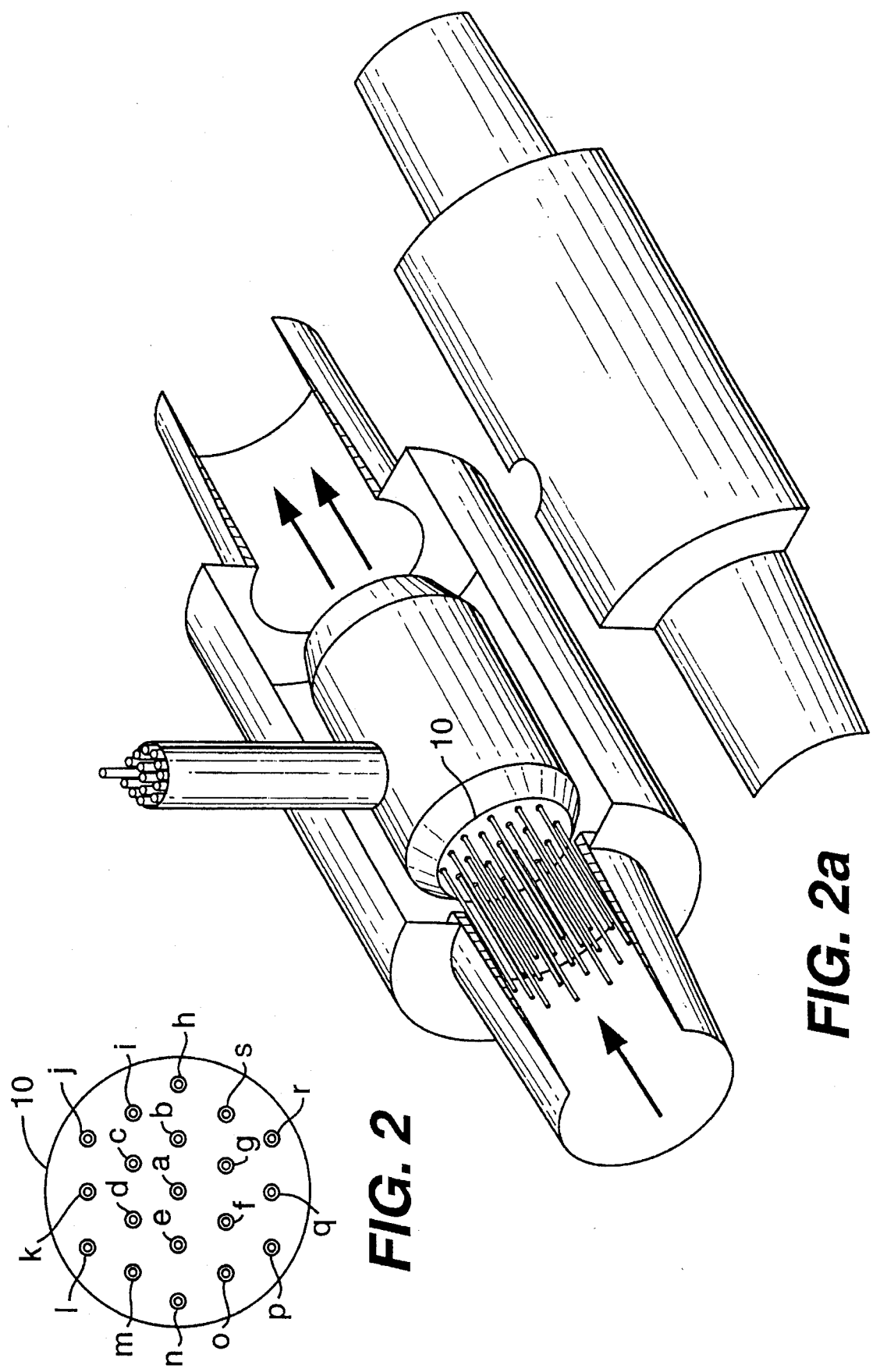
FIG. 2 is a diagram illustrating the placement of electrode within the electrode cluster of the sensor means in accordance with the preferred embodiment of the present invention.

In the preferred embodiment, the electrode cluster 10(a)–(c) consists of 19 Teflon insulated surgical stainless steel wires with uninsulated tips. Other suitable metals may also be used for the wires for the electrode cluster. The wires are preferably 0.19 mm diameter, tapering slightly at the ends, and 25 mm in length. The Teflon coating is preferably 0.005 mm thick. Stainless steel fittings are used for the sides of the electrode cluster. The fittings are pressed in place, and the sensor body is counter bored, so that there is no change in the inside diameter. A shielded cable connects the sensor head to the remainder of the analyzer. The electrode cluster 10(*a*)–(*c*) is configured with a center probe and two outer hexagonal rings of electrodes as shown in FIG. 2. The outer hexagonal ring consisting of probes 10(*h*) to 10(*s*) is rotated 30 degrees out of phase with the inner hexagonal ring consisting of probes 10(*a*) to 10(*g*).

An input multiplexer consisting of 32 channels is connected to said electrode cluster. The channels operate as selector switches and are used to activate a pair of said electrodes in said electrode cluster at any given point in time. The input multiplexer consists of 32 channels, one per electrode.

Figure 3:
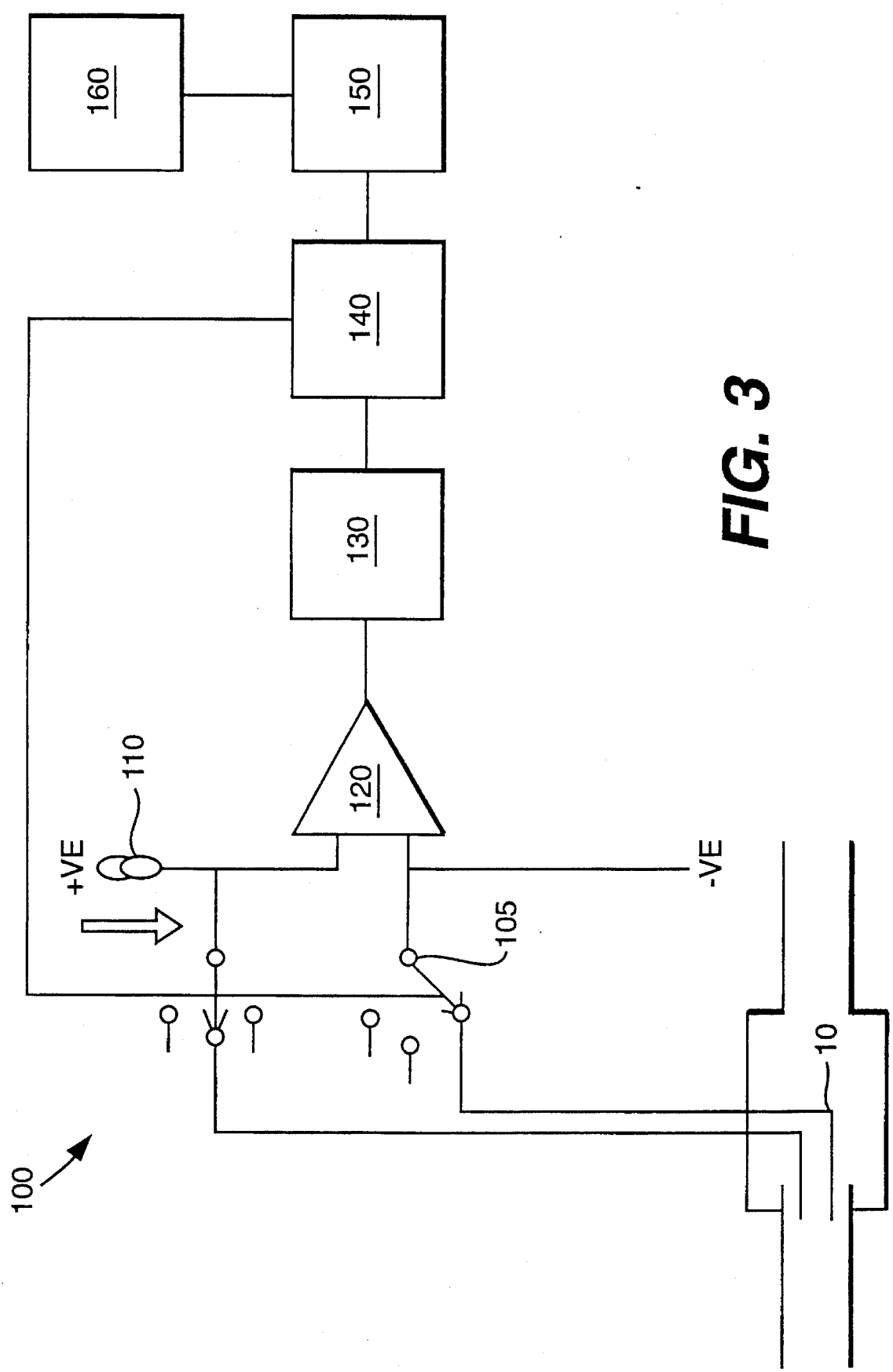
FIG. 3 is a block diagram of the concentration analyzer in accordance with the preferred embodiment of the present invention.

The input multiplexer connects the electrode cluster to a circuit 100 for measuring conductivity as shown in FIG. 3. This circuit 100 repeatedly measures the conductivity difference between the electrodes in the electrode cluster by isolating one pair of electrodes at a time, such as electrode #1 and electrode #2 shown in FIG. 3. The circuit 100 comprises a constant current source 110 connected to said input multiplexer. The conductivity between each activated, selected electrode pair is measured by passing a small electrically isolated constant current from said constant current source 110 through the two activated, selected electrodes. The voltage drop between the electrodes #1 and #2 is measured and is used to indicate fluid conductivity since:

current/voltage=conductivity.

Circuit 100 operates as follows. The input multiplexer selector switches 105 are sent a six bit "sensor code" which identifies the particular pair of electrodes which is to be connected to the constant current source 110. Each input multiplexer channel is normally "open circuit," but any two input multiplexers channels can be activated simultaneously by sending the six bit sensor code to the channel to be connected to the constant current source 110, thus closing the channel and connecting an electrode from the selected electrode pair to the current source 110, and to the other electrode in the electrode pair to be connected to ground. The two electrode sensor heads to be accessed are also connected to an instrumentation amplifier 120 that measures the potential difference between the two accessed electrodes. Independent multiplexers are also connected to the instrumentation amplifier 120 so that errors are not introduced by voltage drops in the current source/sink circuits. The time between accessing or activating any electrode pair is less than one microsecond.

In the preferred embodiment, the input multiplexer is comprised of a 16-channel, dual 8-channel CMOS analog multiplexer, such as the DG406/DG407 multiplexer manufactured by Maxim Integrated Products. The constant current source 120 is comprised of a current mirror comparator to establish a precise fixed constant current. No smoothing capacitance is used in order to ensure rapid response time.

When measuring the potential difference between an electrode pair, the polarity of the applied constant current is alternated once and the two measurements are averaged as follows:

$$\frac{\Delta V1 + \Delta V2}{2} = \text{average potential difference between electrodes.}$$

This technique prevents the electrodes from being electrolytically decomposed and also improves the accuracy of the reading since it is an "oversampling" technique.

After applying the constant current to the electrode pair, the electrode insulation capacitance must be charged before an accurate reading can be obtained. This is done either by introducing a brief delay (approximately 100 microseconds) or by injecting a small charge through the circuit prior to obtaining the voltage reading. The voltage difference between the two electrodes will be inversely proportional to the conductivity of the fluid flowing in the vein, and this voltage is measured by the instrument amplifier 120.

The instrument amplifier 120 has three functions. First, it measures the voltage difference between the electrode pair, for example, electrode #1 and electrode #2. Second, it amplifies that input voltage reading from the electrode pair since the input voltage is lower than the dynamic range of the A/D converter 130 to which the amplifier 120 is connected. Finally, it buffers the output signal since the A/D converter 130 input draws several milliamps of current. In the preferred embodiment, the instrument amplifier is one of 3-op amp design such as the INA114 manufactured by Burr-Brown Corporation.

The A/D converter 130, receives the output from the instrument amplifier 120 and converts the input analog voltage signal to a digital output signal to send to the control CPU 140. In the preferred embodiment, the A/D converter 130 is a BiCMOS serial-output, 14-bit analog-to-digital converter such as the MAX121 manufactured by Maxim Integrated Products. The A/D converter 130 reads the input voltage every four microseconds giving a 250,000 sample/second throughput. The A/D converter 130 has an internal track and hold voltage reference. It generates a signed output, but since the polarity of the input voltage signal is always positive, the signed input signal is converted to an unsigned output signal.

The concentration analyzer of the present invention further includes a control CPU 140. The control CPU 140 stores a region electrode pair file which contains the list of six bit "sensor codes" for activating specific electrode pairs. The control CPU 140 outputs a specific six bit multiplexer control signal to the input multiplexer for selection of a specific electrode pair. Preferably, the control CPU 140 is a 14.7 megahertz 80C451 8-bit computer.

In operation, a user interface program can send the following commands to the control CPU 140:

S: Stop command. Control CPU will open circuit the multiplexers and stop A/D conversions.
  Control CPU will respond with the following string:
  <NULL> S <sensor code> <state>
  The state byte is:
    1 for CPU reset and waiting
    2 for configuration loaded
    3 for error
D: Download command. Control CPU expects this command to be followed by the following message:

-continued

```
         <number of tasks> <delay>
         <electrode #1A> <electrode #1B> . . .
         <electrode #nA> <electrode #nB>
         <checksum of transmission but not D>
      Control CPU will respond with:
         <NULL> D or <NULL>? if error
      (The <delay> byte is a delay in 4.07us
      increments (0–500us) between the excitation of
      the electrode pair and the A/D conversion. It
      will be used if "settling" is required. The
      checksum is only 7 bits (like all data
      transmission) and is calculated to make the
      entire transmission = zero.
      Sending a "D" command will overwrite any
      previous "D" commands, and will put the pump
      back into the stop state.
      Minimum number of tasks is one.)
R:    Run command. This will start the CPU running in a
      continuous loop. It will read the resistance
      of each electrode pair and transmit the
      following information:
         <NULL>
         <electrode pair #1 high byte>
         <electrode pair #1 low byte> . . .
         <electrode pair #n high byte>
         <electrode pair #n low byte>
      (At the end the sequence will repeat.
      A run command will be ignored if there is no
      configuration downloaded.)
G:    Get command. Control CPU expects this command to
      followed by the following message:
         <delay>
         <electrode #A> <electrode #B> . . .
      Control CPU will respond with:
         <NULL> G
         <electrode pair high byte>
         <electrode pair low byte>
V:    Ver command.
      Control CPU will respond with:
         <NULL> Vx.y
(Where x and y are the version and subversion numbers.
Commands other than S,D,R, G or V, parity failures,
checksum failures or too many tasks will cause a
response of <NULL>?
When the control CPU is in run mode, a stop command (S)
must be sent and acknowledged before any further
transmissions can occur. Commands other than S will
cause the control CPU to stop, and respond with a
<NULL>?
The run loop only checks the status of the receiver
periodically, so it may take several ms to respond to
the S command.)
```

Figure 4:
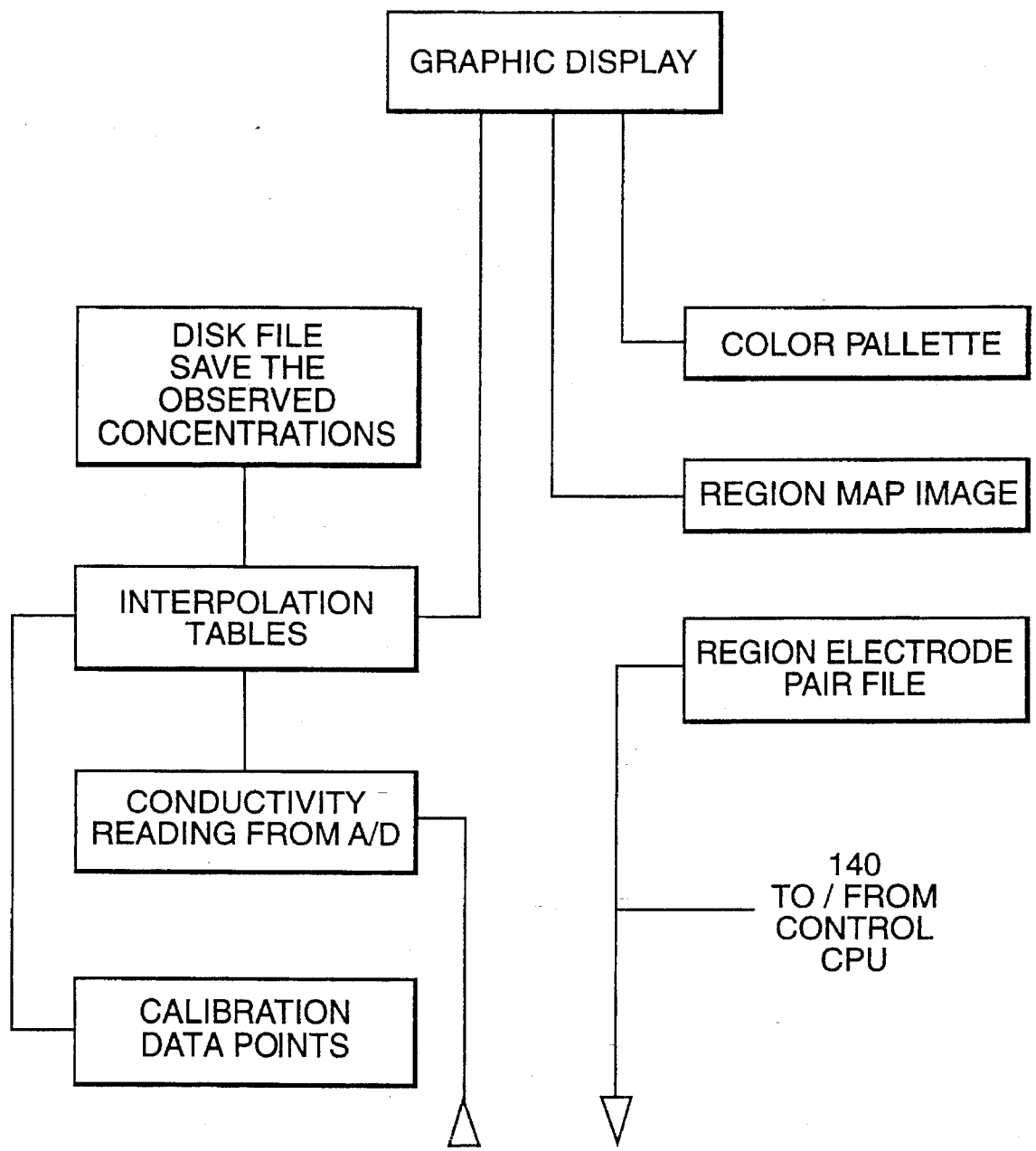
FIG. 4 is a flow chart illustrating the flow of the functions performed by the computing means in accordance with the preferred embodiment of the present invention.

The program is executed as shown in the flow chart of FIG. 4. The user interface program commands the control CPU 140 to read in the region electrode pair file. The six bit sensor codes control the input multiplexer selector switches to select a particular pair of electrodes. The control CPU 140 also receives the output signals from the A/D converter 130. These output signals are serialized and transmitted to the PC 160.

An opto-isolator 150 is connected between the control CPU 140 and to the PC 160. The opto-isolator 150 is used to electrically isolate the serial port that transmits the data to/from the PC 160 to ensure that there is no possibility of common mode leakage current which can cause errors in the conductivity readings.

The user interface program is loaded in the memory of the PC 160 and functions to graphically display the measured fluid conductivity. The user interface program consists of several sub-programs. The code for the "MAIN PROGRAM" is attached as EXHIBIT 1. After initializing the serial port and display, the program will display several subroutine options for selection by the user.

A first sub-routine is entitled "calibrate." When "calibrate" is selected by the user, the user will be required to enter the concentration value of the known, second solution which is to be injected into the artery at the infusion sight 20. The sensor 10 then takes conductivity readings for each electrode pair and these values are recorded in a calibration table as calibration data points. If the sensor 10 must be replaced, a new calibration table must be created.

A second sub-routine is entitled "delete calibration." If an error is made in the calibration of a particular electrode pair, that observation can be deleted without erasing the entire calibration table.

A third sub-routine is entitled "interpolate and run." Once several calibration points have been input into the calibration table, the user interface program can be asked to interpolate the data by running the "interpolate and run" sub-routine. A table-look-up means is used for interpolating the measured converted conductivity/concentration values from the sensor 10 to assign color values to known and recognized concentration values and to store the calibrated concentration values as a particular color value.

The program further includes a sub-routine entitled "load observation." In this sub-routine, actual observations of solution concentration are stored to a disc for later display on the display screen of the PC 160.

A further sub-routine is entitled "single-comparison." This sub-routine allows the simultaneous display of current concentration observations from the sensor 10 next to a playback of earlier observations. The current concentration is graphically displayed in a "contour map" of the cross section of the artery. Colors are used to display varying solution concentrations with the color blue being used for a low concentration and the color red being used for high concentration.

The program further includes a sub-routine entitled "color scale." This subroutine displays on one side of the screen of the monitor of PC 160 a 220 color "rainbow" that indicates the colors corresponding to various concentration values. At either end of the rainbow there will be a number that indicates the percent salinity that color represents. An up and down arrow is located next to each number to allow the percentage limits of the rainbow to be adjusted. After adjusting the color scale, the calibration must be re-interpolated before the sensor 10 may be run again.

Figure 5:
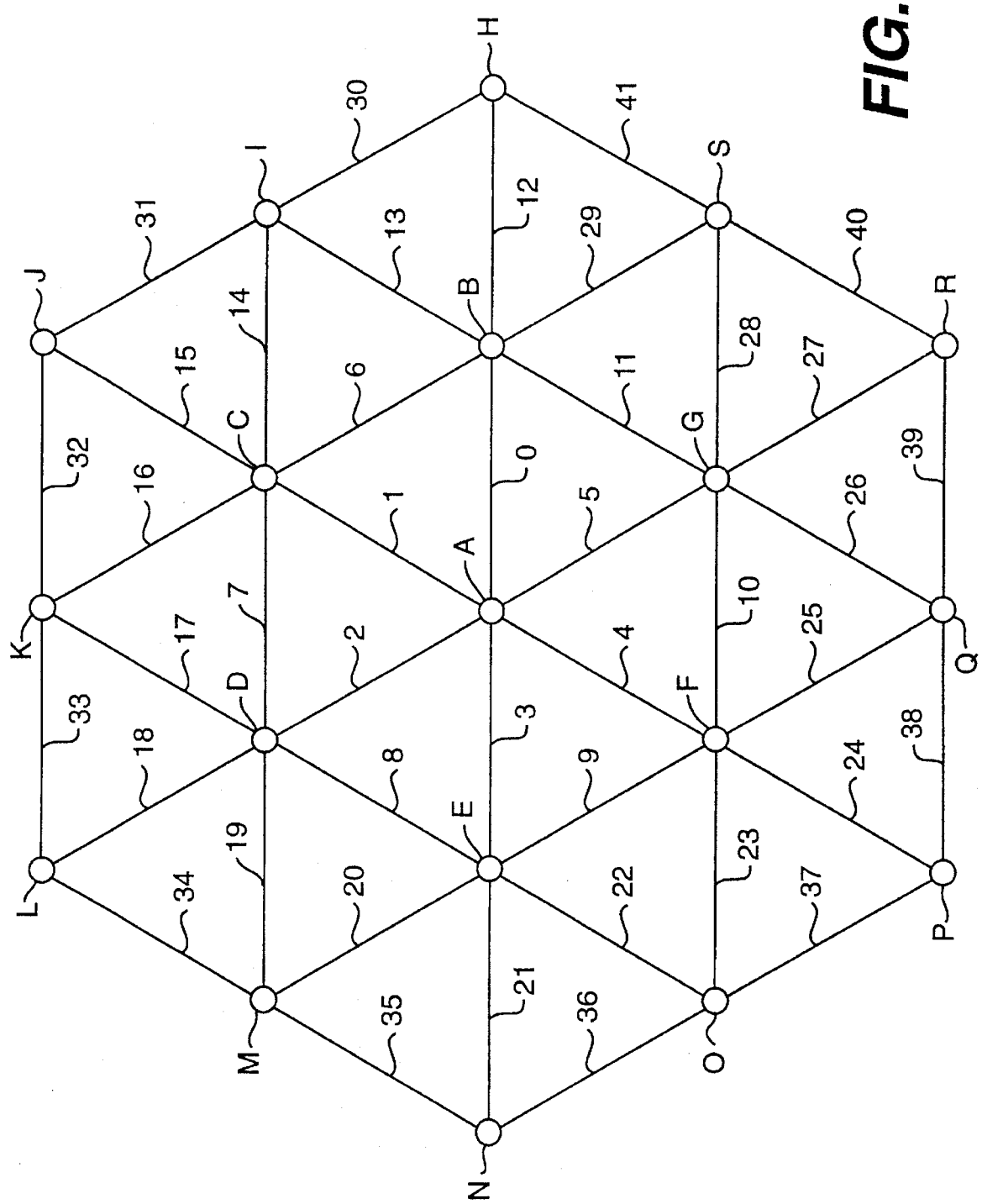
FIG. 5 is a diagram illustrating a region map as would be displayed in accordance with the preferred embodiment of the present invention.

The graphical display sub-routine also includes a region map image display function which identifies the parts of the screen which are reserved for each region of the cross-section of the artery. A typical region map is illustrated in FIG. 5. When displayed on the screen, each region corresponds to a particular pair of sensor electrodes and will be displayed in a color that indicates the solution concentration that the particular pair of electrodes is currently observing. The "SCREEN.CPP" code attached at EXHIBIT 4 fills each region with specified colors corresponding to the concentration value of that region. The image is updated constantly as the fluid flows through the vein and offers a real-time display of the solution concentration in the vein.

It will be apparent to those skilled in the art that various modifications and variations can be made in the apparatus of the present invention without departing from the scope or spirit of the invention. Thus, it is intended that the present invention cover the modifications and variations of this invention provided they come within the scope of the appended claims and their equivalents.

```
;*******************************
; CONDUCTIVITY METER
; VERSION 1.0  2/17/93
; VERSION 2.0  3/24/93    ADDED GET COMMAND
; VERSION 2.1  3/24/93    ADDED VER COMMAND
; VERSION 2.2  3/24/93    FIXED PARITY BIT PROBLEM
; VERSION 2.3  3/24/93    FIXED BUG IN SETTLING DELAY LOOP
; VERSION 2.4  3/24/93    FIXED BUG IN DOWNLOAD RAM OVERFLOW CHECK
; VERSION 2.5  3/25/93    UPGRADED TO NEW PCB PINOUT
; VERSION 2.6  3/25/93    FIXED BUG IN CODE SENSOR READING
; VERSION 2.7  3/30/93    CONVERTED TO A/D CLOCK UNDER CPU CONTROL
; VERSION 2.8  4/2/93     ADDED DESELECT ON INPUT MUX ON STOP & GET COMMAND
; VERSION 2.9  4/2/93     CHANGED SETTLING TIME UNITS TO 20.35usec
; VERSION 3.0  4/3/93     MOVED TASKLIST INTO EXTERNAL RAM TO INCREASE SIZE
;                         NOW UP TO 255 ELECTRODE PAIRS!!
; VERSION 3.1  4/3/93     FIXED RAM CS PROBLEM
; JULIAN WARHURST
;
; HARDWARE: 80C151 @ 14.7456Mhz
;           SERIAL PORT ATTACHED
;
;*******************************

#INCLUDE "80C451.INC"

; MEMORY MAP
; REGISTER 0 (00h)     : MAIN STATE OF CONTROLLER
; REGISTER 1 (01h)     : POINTER TO TASK LIST
; REGISTER 2 (02h)     : SETTLING DELAY
; REGISTER 3 (03h)     : USED TO ACCUMULATE CHECKSUM
; REGISTER 4 (04h)     : USED AS A SCRATCHPAD
; REGISTER 5 (05h)     : USED AS A COUNTER
; REGISTER 7 (07h)     : RESERVED FOR TIMING INTERRUPT DELAY
;
#DEFINE   STATE         R0
#DEFINE   SETTLE_DLY    R2
#DEFINE   ACCUM_CHECK   R3
#DEFINE   SCRATCH       R4
#DEFINE   LOOP_CNT1     R5
#DEFINE   LOOP_CNT2     R6
#DEFINE   IRQ_DELAY     R7

#DEFINE   SUB_VER       '1'
#DEFINE   VERSION       '3'

STACK_BOT    .EQU  008H  ; BOTTOM OF STACK
                         ; 8 BYTES ABOVE RESERVED FOR STACK
                         ; ACALL = 2 BYTES
                         ; TIMER irq = 3 BYTES NUM_TASKS    .EQU  010H  ; NUMBER OF TASKS IN TASK LIST
;                        ; (NOTE EACH TASK IS 2 BYTES LONG)

TASK_BOT     .EQU  02000H ; BOTTOM OF TASK LIST & RAM
TASK_TOP     .EQU  03FFFH ; TOP OF TASK LIST

; SHARED FLAG TABLE
```

```
RCV_ERR_FLG    .EQU    00H     ; SET TO INDICATE A RECIEVE ERROR
MUX_POL        .EQU    01H     ; MULTIPLEXER POLARITY

;    BYTE MAPPED I/O TABLE
MUX_A          .EQU    P1      ; THIS IS PORT 1, UPPER 2 BITS NOT USED
MUX_B          .EQU    P5      ; THIS IS PORT 5, UPPER 2 BITS NOT USED

;    BITMAPED I/O TABLE

;outputs
SCLK           .EQU    P6.4    ; A/D SERIAL CLOCK
CONVST         .EQU    P6.2    ; A/D START (LOW TO START)
WATCHDOG       .EQU    P6.6    ; WATCHDOG STROBE ;inputs
DCLK           .EQU    P6.0    ; A/D DATA CLOCK OUT
SDATA          .EQU    P6.1    ; A/D DATA INPUT
FSTAT          .EQU    P6.3    ; A/D FRAME START
CODE0          .EQU    P4.5    ; SENSOR CODE BIT 0
CODE1          .EQU    P4.4    ; SENSOR CODE BIT 1
CODE2          .EQU    P4.3    ; SENSOR CODE BIT 2
CODE3          .EQU    P4.2    ; SENSOR CODE BIT 3
CODE4          .EQU    P4.1    ; SENSOR CODE BIT 4
CODE5          .EQU    P4.0    ; SENSOR CODE BIT 5

;*************************
;* START OF MAINLINE CODE *
;*************************
;
               .ORG 0000
START          LJMP INITIALIZE

;*********************************************************************
;* THIS IS THE TIMER 0 INTERRUPT                                      *
;* IT IS RESPONSIBLE FOR RUNNING THE PSEUDO TIMER.  THIS IS A         *
;* 50ms TIMER THAT CAN BE SET BY THE INLINE CODE.                     *
;*                                                                    *
;*********************************************************************

.ORG 000BH      ; TIMER 0 INTERRUPT VECTOR

; RELOAD TIMER
                               ; SET TIMER 0 FOR 50ms INTERRUPT
        MOV TL0,#0FFH          ; 14,745,600 / 12 / 61440 = 20 PER SECOND
        MOV TH0,#00FH          ; 61440 = F000h
                               ; FFFFh - F000h = 0FFFh

SETB WATCHDOG          ; STROBE THE WATCHDOG
        CLR  WATCHDOG

PUSH PSW
PSUDO   ;PSEUDO TIMER. A n * 50MS SOFTWARE LOADABLE TIMER USED AS A DELAY
        CJNE IRQ_DELAY,#0,DO_TIMER   ; IF DELAY ALREADY DONE JUST SKIP
        POP PSW
        RETI
DO_TIMER
        DEC IRQ_DELAY                ; DECREMENT DELAY COUNTER
        POP PSW
        RETI
```

```
;******************************************************************
;* THIS IS THE INITIALIZE ROUTINE THAT CONFIGURES THE SYSTEM      *
;******************************************************************
;* NOTE ON WATCHDOG MAINTENANCE:
;* WATCHDOG IS STROBED IN THREE PLACES:
;*          MAINLINE CODE VERY FAST UPDATE
;*          A/D RUN CODE ON COMPLETION OF A FRAME 6ms
;*          IN THE 50ms IRQ WHILE RUNNING SERIAL TIMER DELAYS
;******************************************************************
INITIALIZE
        MOV SP,#STACK_BOT       ;INITIALIZE THE STACK POINTER

MOV TMOD,#00100001B     ;SET TIMER 0 FOR A 16 BIT
                                ;TIMER UNDER INTERNAL CONTROL. (MODE 1)
                                ;LOWER BYTE = 0001
                                ;SET TIMER 1 FOR A 8 BIT AUTORELOAD
                                ;TIMER UNDER INTERNAL CONTROL. (MODE2)
                                ;UPPER BYTE = 0010

; SET TIMER 0 FOR 50ms INTERRUPT
        MOV TL0,#0FFH   ; 14,745,600 / 12 / 61440 = 20 PER SECOND
        MOV TH0,#00FH   ; 61440 = F000h
                        ; FFFFh - F000h = 0FFFh

; SET TIMER 1 FOR A BAUD RATE GENERATOR
        MOV TH1,#0FEH   ; 38400 BAUD
                        ; 256 - (MULT * FOSC)/(384*BAUDRATE)
                        ; 256 - (2 * 14,745,600)/(384*38400) = 254 = FEh

MOV PCON,#10000000B ; SET BAUD RATE MULTIPLY TO 2
        MOV SCON,#01010010B ; SERIAL PORT MODE 1, 8 BIT UART
                            ; SET TRANMITTER READY FLAG
                            ; ENABLE THE RECIEVER

MOV TCON,#01010000B ; SET TIMER 0 AND 1 TO RUN.
        MOV IRQ_DELAY,#0    ; SET TIMER TO ZERO
        MOV IE,#10000000B   ; ENABLES ALL INTERRUPTS BUT ALL MASKED OFF
                            ; TIMER 0 (50ms) WILL BE INTERRUPT DRIVEN
                            ; SERIAL PORT NOT INTERRUPT DRIVEN
        MOV PSW,#0          ; MAKE SURE THAT REGISTER BANK 0 IS SELECTED

MOV STATE,#WAIT_N_CFG
                ; NOTE!! REGISTER 0 IS RESERVED FOR THE MAIN STATE
                ; OF THE SYSTEM
                ; INITIALIZE THE MAIN STATE TO WAITING WITH NO CONFIG

MOV NUM_TASKS,#0
                ; NUMBER OF TASKS IN LIST
                ; NONE INITIALLY

MOV DPTR,#TASK_BOT
                ; NOTE DPTR IS THE TASK POINTER
                ; SET TO BOTTOM OF LIST, BUT DOSEN'T REALLY MATTER
                ; SINCE ALWAYS RESET BEFORE USE

MOV SETTLE_DLY,#0
                ; NOTE!! REGISTER 2 IS THE SETTLING DELAY
                ; ZERO INITIALLY (BUT ACTUALLY DOESN'T MATTER
                ; SINCE IT IS NOT USED UNLESS TASKS ARE > 0 )
```

```
        MOV MUX_A,#0    ; DESELECT INPUT MULTIPLEXERS
        MOV MUX_B,#0

;*****************************************************************
;* PROGRAM ORGAINIZATION:
;*   THERE ARE THREE MAJOR BLOCKS:
;*   1)  THE MAIN LOOP WHICH WAITS FOR INTERRUPT TO EXIT
;*   2)  THE RECIEVER WHICH BREAKS EITHER THE MAIN OR RUN LOOP
;*   3)  THE RUN LOOP THAT READS THE A/D AND TRANSMITS IT.
;*
;*   PROGRAM STATES:
;*        STATE 0 = RUNNING
;*        STATE 1 = WAITING WITH NO CONFIGURATION
;*        STATE 2 = WAITING WITH CONFIGURATION LOADED
;*        STATE 3 = ERROR STATE
;*****************************************************************
RUNNING      .EQU   0
WAIT_N_CFG   .EQU   1
WAIT_W_CFG   .EQU   2
ERROR        .EQU   3
;*****************************************************************
;* PROGRAM STARTS IN MAIN AND RETURNS WHENEVER WAITING
;*****************************************************************

MAIN
        ; CHECK IF A CHARACTER HAS BEEN RECIEVED
        ; POLL RECIEVER
        JB SCON.0,RECIEVER  ; IF CHARACTER IS RECIEVED DO RECIEVER
        SETB WATCHDOG       ; STROBE THE WATCHDOG
        CLR  WATCHDOG
        SJMP MAIN           ; TERMINAL LOOP

;*****************************************************************
;* BRANCHES TO RECIEVER WHENEVER FIRST CHARACTER IS RECIEVED
;*****************************************************************

RECIEVER
        MOV A,SBUF       ; GET RECIEVED CHARACTER, FIRST CHAR INDICATES COMMAND
        CLR SCON.0       ; RE-ENABLE THE RECIEVER
        JB P,SND_ERR_MSG ; IF NOT EVEN PARITY THEN ERROR
        ;JNB P,SND_ERR_MSG ; IF NOT ODD PARITY THEN ERROR
        ANL A,#07FH      ; MASK OFF PARITY BIT ONCE VERIFIED

CJNE A,#'S',NOT_STOP  ; CHECK FOR STOP COMMAND
        AJMP RCV_STOP
NOT_STOP
        CJNE A,#'D',NOT_DOWNL ; CHECK FOR DOWNLOAD COMMAND
        AJMP RCV_DOWNL
NOT_DOWNL
        CJNE A,#'R',NOT_RUN   ; CHECK FOR RUN COMMAND
        AJMP RCV_RUN
NOT_RUN
        CJNE A,#'G',NOT_GET   ; CHECK FOR GET COMMAND
        AJMP RCV_GET
NOT_GET
        CJNE A,#'V',NOT_VER   ; CHECK FOR VER COMMAND
        AJMP RCV_VER

NOT_VER                       ; IF NO OTHER COMMAND RECIEVED THEN MUST BE ERROR
```

```
SND_ERR_MSG         ; IN EITHER CASE, SEND <NULL> ?
        MOV A,#0    ; SEND A NULL
        ACALL SEND
        MOV A,#'?'  ; SEND A '?'
        ACALL SEND
        CLR RCV_ERR_FLG
        SJMP MAIN

;******************************************************************

RCV_STOP            ; RECEIVED A STOP MESSAGE
        CJNE STATE,#RUNNING,SEND_STOP ; CHECK IF RUNNING
        MOV STATE,#WAIT_W_CFG   ; WAS RUNNING SET STATE TO WAIT WITH CONFIG
                                ; NO OTHER STATE REQUIRES A CHANGE OF STATE
SEND_STOP                       ; RESPOND WITH STOP MESSAGE
        MOV A,#0        ; SEND A NULL
        ACALL SEND
        MOV A,#'S'      ; SEND A 'S'
        ACALL SEND
        MOV A,#0        ; PUT SENSOR CODE INTO THE ACCUMULATOR
        MOV C,CODE0
        MOV ACC.0,C
        MOV C,CODE1
        MOV ACC.1,C
        MOV C,CODE2
        MOV ACC.2,C
        MOV C,CODE3
        MOV ACC.3,C
        MOV C,CODE4
        MOV ACC.4,C
        MOV C,CODE5
        MOV ACC.5,C
        ACALL SEND      ; ... THEN SEND THE SENSOR CODE
        MOV A,STATE     ; SEND THE STATE BYTE
        ACALL SEND
        MOV MUX_A,#0    ; DESELECT INPUT MULTIPLEXERS
        MOV MUX_B,#0
        SJMP MAIN

;******************************************************************

RCV_RUN             ; RECEIVED A RUN MESSAGE
        CJNE STATE,#WAIT_W_CFG,SND_ERR_MSG  ; MUST BE WAITING WITH CONFIGURATION
                                            ; LOADED IN ORDER TO RUN
        MOV STATE,#RUNNING
        AJMP RUN    ; ENTER THE RUN LOOP

;******************************************************************

RCV_DOWNL           ; RECIEVED A DOWNLOAD MESSAGE
                    ; DO DOWNLOAD FUNCTION
        MOV ACCUM_CHECK,#0 ; CLEAR CHECKSUM ACCUMULATOR
        CLR RCV_ERR_FLG    ; CLEAR RECIEVER ERROR FLAG
        ACALL GET          ; GET THE NUMBER OF TASKS
        MOV NUM_TASKS,A

ACALL GET          ; GET THE SETTLING DELAY
        MOV SETTLE_DLY,A
```

```
        MOV DPTR,#TASK_BOT      ; INITIALIZE TASK POINTER
        MOV A,NUM_TASKS
        MOV LOOP_CNT1,A         ; GET LOOP COUNTER
        JZ VERIFY_RX_OK         ; IF NO TASKS TO DO THEN EXIT
CREATE_TASK_TABLE
        ; GET ELECTRODE A
        ACALL GET
        MOVX @DPTR,A
        INC DPTR
        ; GET ELECTRODE B
GET_ELECT_B
        ACALL GET
        MOVX @DPTR,A
        INC DPTR

DL_LOOP   ; CHECK IF ALL ENTRIES COPIED
        DJNZ LOOP_CNT1,CREATE_TASK_TABLE

VERIFY_RX_OK
        ; CHECK FOR RECEIVER PARITY ERROR
        JNB RCV_ERR_FLG,CHECK_DL_CKSUM
DL_ERROR
        MOV STATE,#WAIT_N_CFG   ; CHANGE STATUS TO NO CONFIG
        AJMP SND_ERR_MSG
CHECK_DL_CKSUM
        ACALL GET               ; GET THE CHECKSUM
        MOV A,ACCUM_CHECK
        ANL A,#01111111B        ; 7 BIT CHECKSUM BECAUSE 7 BIT DATA
        JZ SEND_DL_ACK
        MOV STATE,#WAIT_N_CFG   ; CHANGE STATUS TO NO CONFIG
        AJMP SND_ERR_MSG
SEND_DL_ACK
        MOV A,#0      ; SEND A NULL
        ACALL SEND
        MOV A,#'D'    ; SEND A 'D'
        ACALL SEND
        MOV STATE,#WAIT_W_CFG ; UPDATE CONFIGURATION
        AJMP MAIN

;****************************************************************
RCV_VER
        MOV A,#0      ; SEND A NULL
        ACALL SEND
        MOV A,#'V'    ; SEND A 'V'
        ACALL SEND
        MOV A,#VERSION   ; SEND VERSION #
        ACALL SEND
        MOV A,#'.'    ; SEND PERIOD
        ACALL SEND
        MOV A,#SUB_VER   ; SEND SUB VERSION #
        ACALL SEND
        AJMP MAIN

;****************************************************************

RCV_GET
        CLR RCV_ERR_FLG    ; CLEAR RECIEVER ERROR FLAG
        ACALL GET          ; GET THE SETTLING DELAY
        MOV B,A            ; SAVE IN B REGISTER
```

```
        ; GET ELECTRODE A
        ACALL GET
        MOV MUX_A,A    ; SETUP MUX A
        ; GET ELECTRODE B
        ACALL GET
        MOV MUX_B,A    ; SETUP MUX B

; CHECK FOR RECEIVER PARITY ERROR
        JNB RCV_ERR_FLG,OK_TO_GET
        AJMP SND_ERR_MSG

OK_TO_GET
        SETB CONVST    ; MAKE SURE A/D IS SETUP
        SETB SDATA
        MOV LOOP_CNT1,#18   ; FLUSH A/D SERIAL PORT
FLUSH1
        SETB SCLK      ; 18 CLOCKS WHICH IS EXCESSIVE
        CLR SCLK
        DJNZ LOOP_CNT1,FLUSH1
                       ; LEAVES LOOP WITH CLOCK LOW

; RUN SETTLING DELAY IF REQUIRED
        MOV A,B
SETTLE
        JZ START_AD1           ; 24 CYCLES : IF ZERO GO STRAIGHT TO CONVERT
        MOV LOOP_CNT2,#9       ; 24 CYCLES
SL1
        DJNZ LOOP_CNT2,SL1     ; 216 CYCLES
        DEC A                  ; 12 CYCLES : 300/14745600 = 20.35us
        SJMP SETTLE            ; 24 CYCLES

START_AD1
        CLR CONVST             ; START A/D CONVERTOR
        SETB SCLK              ; RISING EDGE OF FIRST CLOCK
        SETB CONVST            ; RESET CONVST LINE
        CLR SCLK               ; FALLING EDGE OF FIRST CLOCK

; SERIALLY READ FIRST 7 BITS
        MOV LOOP_CNT2,#7
GET_AD_MSB1
        SETB SCLK              ; MAKES A/D PUT DATA ON PIN
        MOV C,SDATA            ; PUT DATA INTO CARRY
        RLC A                  ; SHIFT LEFT INTO ACCUM
        CLR SCLK               ;
        DJNZ LOOP_CNT2,GET_AD_MSB1

MOV B,A                ; SAVE IN B REGISTER

; SERIALLY READ NEXT 7 BITS
        MOV LOOP_CNT2,#7
GET_AD_LSB1
        SETB SCLK              ; MAKES A/D PUT DATA ON PIN
        MOV C,SDATA            ; PUT DATA INTO CARRY
        RLC A                  ; SHIFT LEFT INTO ACCUM
        CLR SCLK               ;
        DJNZ LOOP_CNT2,GET_AD_LSB1

MOV SCRATCH,A          ; SAVE IN SCRATCH REGISTER

; FLUSH LAST 2 BITS
```

```
        SETB SCLK               ; MAKES A/D PUT DATA ON PIN
        CLR  SCLK
        SETB SCLK               ; MAKES A/D PUT DATA ON PIN
        CLR  SCLK

SEND_GET_ACK
        MOV A,#0        ; SEND A NULL
        ACALL SEND
        MOV A,#'G'      ; SEND A 'G'
        ACALL SEND
        MOV A,B         ; GET MSB
        ACALL SEND
        MOV A,SCRATCH   ; GET LSB
        ACALL SEND

MOV MUX_A,#0    ; DESELECT INPUT MULTIPLEXERS
        MOV MUX_B,#0
        AJMP MAIN

;****************************************************************
;* SEND WILL TRANSMIT THE CONTENTS OF THE ACCUMULATOR
;* FIRST CHECKS IF TRANSMITTER IS READY
;* IF READY SENDS CHARACTER IN ACC
;* IF NOT READY SETS UP 100ms DELAY
;* NOW SENDS IF TRANSMITTER BECOMES READY, OR IF 100ms TIMES OUT
;****************************************************************
SEND
        SETB WATCHDOG           ; STROBE THE WATCHDOG
        CLR  WATCHDOG

ANL A,#07FH             ; MUST NEVER GET PASSED 8 BIT DATA, BUT
                                ; MASKS OFF BIT 8 JUST IN CASE.

MOV C,P                 ; GET PARITY FLAG, 1 IF ODD, 0 IF EVEN
        ;CPL C                  ; THIS GIVES ODD PARITY
        MOV ACC.7,C             ; MOV PARITY INTO BIT 7 OF TRANSMIT BYTE
        JNB SCON.1,WAIT_FOR_TX  ; WAIT FOR TRANSMITTER FREE
        MOV SBUF,A              ; SEND ACCUMULATOR
        CLR SCON.1              ; INDICATE TRANSMITTER BUSY
        RET

WAIT_FOR_TX                     ; SINCE NOT READY SETUP 100ms TIMER
        SETB ET0                ; ENABLE INTERRUPT (THIS WILL CAUSE IMMED. IRQ)
        MOV IRQ_DELAY,#2        ; SET 2 X 50ms
WAIT_TX_LOOP
        JBC SCON.1,DO_SEND      ; IF SERIAL PORT READY SEND
                                ; ALSO INDICATE TRANSMITTER BUSY
        CJNE IRQ_DELAY,#0,WAIT_TX_LOOP ; WAIT IF TIMER NOT 0
DO_SEND
        MOV SBUF,A              ; SEND ACCUMULATOR
        CLR ET0                 ; DISABLE TIMER INTERRUPT
        RET

;****************************************************************
;* GET WILL RECIEVE A BYTE, AND PUT IN ACCUM
;* FIRST CHECKS IF RECIEVER HAS CHAR
;* IF CHAR THEN PUTS CHAR INTO ACC
;* IF NOT READY SETS UP 250ms DELAY
;* IF TIMES OUT THEN RETURNS A <NULL> WITH ODD PARITY (80H)
;****************************************************************
;
```

```
GET
        JB SCON.0,DO_GET            ; IF RECIEVER HAS CHARACTER, TAKE
                                    ; ELSE WAIT FOR CHAR
WAIT_FOR_RX                         ; SINCE NOT READY SETUP 250ms TIMER
        SETB ET0                    ; ENABLE INTERRUPT (THIS WILL CAUSE IMMED. IRQ)
        MOV IRQ_DELAY,#5            ; SET 5 X 50ms
WAIT_RX_LOOP
        JB SCON.0,DO_GET_DI         ; IF CHAR READY THEN GET ALSO DISABLES INTERRUPT

CJNE IRQ_DELAY,#0,WAIT_RX_LOOP ; WAIT IF TIMER NOT 0
GET_TIMED_OUT                       ; 250ms EXPIRED
        MOV A,#0                    ; RETURN <NULL>
        SETB RCV_ERR_FLG            ; SET ERROR FLAG
        CLR ET0                     ; DISABLE TIMER INTERRUPT
        RET
DO_GET_DI
        CLR ET0                     ; DISABLE TIMER INTERRUPT
DO_GET
        MOV A,SBUF                  ; GET CHARACTER
        CLR SCON.0                  ; CLEAR FLAG
        JNB P,GET_OK                ; CHECK FOR PARITY ERROR
        SETB RCV_ERR_FLG
GET_OK
        ANL A,#07FH                 ; MASK OFF PARITY ONCE CHECKED
        MOV SCRATCH,A               ; SAVE CHARACTER IN SCRATCHPAD
        ADD A,ACCUM_CHECK           ; ADD TO CHECKSUM
        MOV ACCUM_CHECK,A           ; ACCUMULATE
        MOV A,SCRATCH               ; RESTORE CHARACTER
        RET

;******************************************************************

RUN
        CLR MUX_POL      ; CLEAR THE MUX POLARITY BIT
        SETB CONVST      ; MAKE SURE A/D IS SETUP
        SETB SDATA
        MOV LOOP_CNT1,#18   ; FLUSH A/D SERIAL PORT
FLUSH
        SETB SCLK           ; 18 CLOCKS WHICH IS EXCESSIVE
        CLR SCLK
        DJNZ LOOP_CNT1,FLUSH
                            ; LEAVES LOOP WITH CLOCK LOW

RUN_LOOP
        MOV A,#0            ; SEND A NULL TO START
        ACALL SEND
        MOV LOOP_CNT1,NUM_TASKS ; GET NUMBER OF TASKS IN COUNTER
        MOV DPTR,#TASK_BOT     ; SET POINTER TO BOTTOM OF TASK LIST

; CHECK THE MUX POLARITY
        JBC MUX_POL,MUX_INVERSE ; REVERSE POLARITY OF MUX BIT
            ; PRELOAD THE MUXES NORMAL ORDER
        MOVX A,@DPTR            ; GET MUX A
        MOV MUX_A,A             ; SETUP MUX A
        INC DPTR
        MOVX A,@DPTR            ; GET MUX B
        MOV MUX_B,A             ; SETUP MUX B
        INC DPTR
        SETB MUX_POL
        SJMP RUN_SETTLE_DELAY
```

```
MUX_INVERSE
        ; PRELOAD THE MUXES REVERSE ORDER
        MOVX A,@DPTR
        MOV MUX_B,A            ; SETUP MUX B
        INC DPTR
        MOVX A,@DPTR
        MOV MUX_A,A            ; SETUP MUX A
        INC DPTR

RUN_SETTLE_DELAY
        ; RUN SETTLING DELAY IF REQUIRED
        MOV A,SETTLE_DLY
WAIT_TO_SETTLE
        JZ CHECK_STOP          ; 24 CYCLES : IF ZERO GO STRAIGHT TO CONVERT
        MOV LOOP_CNT2,#9       ; 24 CYCLES
SL2
        DJNZ LOOP_CNT2,SL2     ; 216 CYCLES
        DEC A                  ; 12 CYCLES : 300/14745600 = 20.35us
        SJMP WAIT_TO_SETTLE    ; 24 CYCLES :

CHECK_STOP
        ; CHECK IF RECIEVER HAS A CHARACTER
        JNB SCON.0,START_AD;
        LJMP RECIEVER          ; GO TO RECIEVER IF THERE IS AS CHARACTER WAITING

START_AD
        CLR CONVST             ; START A/D CONVERTOR
        SETB SCLK              ; RISING EDGE OF FIRST CLOCK
        SETB CONVST            ; RESET CONVST LINE
        CLR SCLK               ; FALLING EDGE OF FIRST CLOCK

; SERIALLY READ FIRST 7 BITS

MOV LOOP_CNT2,#7
GET_AD_MSB
        SETB SCLK              ; MAKES A/D PUT DATA ON PIN
        MOV C,SDATA            ; PUT DATA INTO CARRY
        RLC A                  ; SHIFT LEFT INTO ACCUM
        CLR SCLK               ;
        DJNZ LOOP_CNT2,GET_AD_MSB

; PARITY CORRECT AND SAVE
        MOV C,P                ; GET PARITY FLAG, 1 IF ODD, 0 IF EVEN    29
        MOV ACC.7,C            ; MOV PARITY INTO BIT 7 OF TRANSMIT BYTE  30
        MOV SCRATCH,A          ; SAVE IN SCRATCH REGISTER                31

; SERIALLY READ NEXT 7 BITS
        MOV LOOP_CNT2,#7
GET_AD_LSB
        SETB SCLK              ; MAKES A/D PUT DATA ON PIN
        MOV C,SDATA            ; PUT DATA INTO CARRY
        RLC A                  ; SHIFT LEFT INTO ACCUM
        CLR SCLK               ;
        DJNZ LOOP_CNT2,GET_AD_LSB

; CHECK IF TRANSMITTER FREE   59 * .8138us = 48us (261us FOR XMIT)
WAIT_BYTE1
        JBC SCON.1,SEND_BYTE1  ;
        SJMP WAIT_BYTE1
SEND_BYTE1
```

```
        MOV SBUF,SCRATCH        ; SEND OUT MSBYTE OF A/D

; FLUSH LAST 2 BITS WHILE WAITING
        SETB SCLK               ; MAKES A/D PUT DATA ON PIN
        CLR SCLK
        SETB SCLK               ; MAKES A/D PUT DATA ON PIN
        CLR SCLK

; PRELOAD NEXT MUX JOB WHILE WAITING
            ; CHECK THE MUX POLARITY
        JNB MUX_POL,MUX_INVERSE1
            ; PRELOAD THE MUXES NORMAL ORDER
        MOVX A,@DPTR
        MOV MUX_A,A       ; SETUP MUX A
        INC DPTR
        MOVX A,@DPTR
        MOV MUX_B,A       ; SETUP MUX B
        INC DPTR
        SJMP RCV_CHECK
MUX_INVERSE1
            ; PREOAD THE MUXES REVERSE ORDER
        MOVX A,@DPTR
        MOV MUX_B,A       ; SETUP MUX B
        INC DPTR
        MOVX A,@DPTR
        MOV MUX_A,A       ; SETUP MUX A
        INC DPTR

RCV_CHECK
        ; CHECK IF RECIEVER HAS A CHARACTER WHILE WAITING
        JNB SCON.0,PARITY_LSBYTE
        LJMP RECIEVER           ; GO TO RECIEVER IF THERE IS AS CHARACTER WAITING

PARITY_LSBYTE
        ; PARITY CORRECT LSBYTE
        MOV C,P                 ; GET PARITY FLAG, 1 IF ODD, 0 IF EVEN
        MOV ACC.7,C             ; MOV PARITY INTO BIT 7 OF TRANSMIT BYTE
WAIT_BYTE2
        JBC SCON.1,SEND_BYTE2
        SJMP WAIT_BYTE2
SEND_BYTE2
        MOV SBUF,A              ; SEND OUT LSBYTE OF A/D

DJNZ LOOP_CNT1,GET_NEXT_TASK

; RESTART ENTIRE PACKAGE
        AJMP RUN_LOOP

GET_NEXT_TASK
        SETB WATCHDOG           ; STROBE THE WATCHDOG
        CLR  WATCHDOG
        AJMP RUN_SETTLE_DELAY

;****************************************************************

.END
```

```cpp
// ~ IDUCT.CPP
// Last revised 3/28/93
// This program communicates with the conductivity analizer to both
// download configuration information and display measurements.
// A configuration file for the sensor to be used must be present for this
// program to run.

#include <stdio.h>
#include <stdlib.h>
#include <alloc.h>
#include <dos.h>
#include <conio.h>
include <math.h>

// function prototypes from screen.cpp
int    GetMouseX(void);   // function prototypes
int    GetMouseY(void);
int    AnyButton(void);
void   HideCursor(void);
void   ShowCursor(void);
void   VGAgraphics(void);
void   VGAText(void);
void   PutPixel(int,int,char);
void   BlankLine(int);
void   ClearScreen(void);
void   setpalette(void);
void   PlotCSA(char*,unsigned int*);

// function prototypes from serial.cpp
void   SetupCOM1(void);
void   OpenSerialBuffered(void);
void   OpenSerialRunTime(int);
int    GetDataTable(int);
void   ClearCirBuf(void);
void   outCOM1(char);
int    CommError(void);
int    CirBufNotEmpty(void);
char   GetCirBuf();
void   CloseSerial();

char copywrite[32] = {"COPYRIGHT 1993 JULIAN WARHURST\0"};
char sensorcode = 255;

// these are the remote states
#define  DEAD   0
#define  N_CFG  1
#define  CFG    2
#define  ERROR  3
char RemoteState = 0;

// these are the program run states
#define  WAIT  0
#define  CAL   1
#define  INT   2
#define  RUN   3
#define  QUIT  4
int SystemState = WAIT;

#define  ELECT_PAIR  70    // max number of electrode pairs
```

```c
#define VID_TABLE   5000    // max size of lookup table
int    radius = 5;          // radius of circle on screen
int    LengthLookup = 0;    // length of lookup table
int    NumRegions   = 0;    // number of electrode pairs
char   DisplayData[ELECT_PAIR];
unsigned int  Lookup[VID_TABLE+1];
char   Electrodes[ELECT_PAIR][2];
int    CfgOK = 0;           // configuration OK flag
char   ElectrodeDelay = 0;  // delay time to be downloaded //*******************************************************************
// BootRemote establishes communication via the serial link with the
// conductivity meter.

int BootRemote(void)
{
int returnval = 0;
SetupCOM1();
OpenSerialBuffered();
ClearCirBuf();
outCOM1('S');   // send a stop command
delay(250);     //wait 250ms for remote to respond if(CommError())    // check for comm errors
   {returnval = 2;} if(!returnval && !CirBufNotEmpty()) // buffer is empty
   {returnval = 1;} if(!returnval) // therefore no errors
   {
   if(GetCirBuf() != NULL)
       {returnval = 2;} if(GetCirBuf() != 'S')
       {returnval = 2;}

GetCirBuf(); // purge sensor code if(GetCirBuf() == 3)
       {returnval = 3;}
   }
return(returnval);
} // end of BootRemote
//*******************************************************************
// ShowVersion displays the version number of the conductivity meter void ShowVersion(void)
{
ClearCirBuf();
outCOM1('V');   // send a version command
delay(100);     //wait 250ms for remote to respond if(CirBufNotEmpty()) // buffer is not empty
   {
   printf("Connection established, Conductivity Meter Version ");
   GetCirBuf(); // purge null
   GetCirBuf(); // purge V
   putch(GetCirBuf()); // display version
```

```
      putch(GetCirBuf()); // display period
      putch(GetCirBuf()); // display sub-version
      delay(1250);
      }
} // end of ShowVersion //*********************************************************************
// GetRemoteState   reads the sensor code and state byte
// returns the remote state, plus loads the state byte and sensor code byte.
// Will return a 0 if unable to communicate.

int GetRemoteState(void)
{
int error = 0;

ClearCirBuf();
outCOM1('S');  // send a stop command
delay(250);    //wait 250ms for remote to respond error = CommError();    // check for comm errors
if(error)
    {RemoteState = 0;} if(!error && !CirBufNotEmpty()) // buffer is empty
    {
    RemoteState = 0;
    error = 1;
    } if(!error)
    {
    if(GetCirBuf() != NULL)
        {error = 2;} if(GetCirBuf() != 'S')
        {error = 2;} if(!error)
        {
        sensorcode = GetCirBuf();
        RemoteState = GetCirBuf();
        }
    }
return(RemoteState);
} // end of GetRemoteState

//********************************************************************* void fatalerror(int error)
{
switch(error)
    {
    case 0:  // no error, no message
        break;

case 1:  // could not find conductivity meter
        printf("COULD NOT ESTABLISH COMMUNICATION ON COM1 !\n");
        printf("Make sure serial cable is atached to conductivity meter and that A
        printf("power is turned on.");
        break;
```

```c
#define VID_TABLE   5000    // max size of lookup table
int     radius = 5;         // radius of circle on screen
int     LengthLookup = 0;   // length of lookup table
int     NumRegions   = 0;   // number of electrode pairs
char    DisplayData[ELECT_PAIR];
unsigned int  Lookup[VID_TABLE+1];
char    Electrodes[ELECT_PAIR][2];
int     CfgOK = 0;  // configuration OK flag
char    ElectrodeDelay = 0;  // delay time to be downloaded //*******************************************************************
// BootRemote establishes communication via the serial link with the
// conductivity meter.

int BootRemote(void)
{
int returnval = 0;
SetupCOM1();
OpenSerialBuffered();
ClearCirBuf();
outCOM1('S');  // send a stop command
delay(250);    //wait 250ms for remote to respond if(CommError())   // check for comm errors
   {returnval = 2;} if(!returnval && !CirBufNotEmpty()) // buffer is empty
   {returnval = 1;} if(!returnval) // therefore no errors
   {
   if(GetCirBuf() != NULL)
      {returnval = 2;} if(GetCirBuf() != 'S')
      {returnval = 2;}

GetCirBuf(); // purge sensor code if(GetCirBuf() == 3)
      {returnval = 3;}
   }
return(returnval);
} // end of BootRemote
//*******************************************************************
// ShowVersion displays the version number of the conductivity meter void ShowVersion(void)
{
ClearCirBuf();
outCOM1('V');  // send a version command
delay(100);    //wait 250ms for remote to respond if(CirBufNotEmpty()) // buffer is not empty
   {
   printf("Connection established, Conductivity Meter Version ");
   GetCirBuf(); // purge null
   GetCirBuf(); // purge V
   putch(GetCirBuf()); // display version
```

```
    switch(version[8])
        {
        case '1':
            fseek(sensorfile,0,SEEK_CUR);  // then get circle radius
            fread(&radius,sizeof(radius),1,sensorfile);

fseek(sensorfile,0,SEEK_CUR);  // then get Length of lookup table
            fread(&LengthLookup,sizeof(LengthLookup),1,sensorfile);

fseek(sensorfile,0,SEEK_CUR);  // then get the number of regions
            fread(&NumRegions,sizeof(NumRegions),1,sensorfile);

fseek(sensorfile,0,SEEK_CUR);  // Now read in electrode table
            fread(Electrodes,ELECT_PAIR*2,1,sensorfile);  // read the lookup table fseek(sensorfile,0,SEEK_CUR);  // Now read in the screen lookup table
            fread(Lookup,LengthLookup*sizeof(LengthLookup),1,sensorfile);

returnval = 1;   // signal all is OK
            break;

default:
            returnval = -2;  // signal unknown sensor file version
            break;
        }
    fclose(sensorfile);
    }
return(returnval);
} // end of LoadConfigFile //**********************************************************************
// Download function
// Reads the electrode list information and converts it to the scan codes
// for downloading to the Remote unit.
// Returns a 0 on success or -1 if error int DownLoad()
{
int returnval = 0;
int i;
char c;
char checksum = 0;

ClearCirBuf();  // clear recieve buffer outCOM1('D');   // send a download command checksum = checksum + (char)NumRegions;
outCOM1((char)NumRegions);

checksum = checksum + ElectrodeDelay;
outCOM1(ElectrodeDelay);

for(i=0;i!=NumRegions;i++)
    {
    // get first electrode
    c = Electrodes[i][0];
    // perform translation for enable control of input muxes
    if(c<15)
        {c = c|0x10;}
```

```
    else
        {c = c&0x0F;
         c = c|0x20;}
    checksum = checksum + c;
    outCOM1(c);

// get second electrode
    c = Electrodes[i][1];
    // perform translation for enable control of input muxes
    if(c<15)
        {c = c|0x10;}
    else
        {c = c&0x0F;
         c = c|0x20;}
    checksum = checksum + c;
    outCOM1(c);
    }

// send the checksum.  Designed to make total = 0 checksum = (256-checksum) & 0x7f; // must be 7 bit
outCOM1(checksum);

delay(250);     //wait 250ms for remote to respond if(CommError())    // check for comm errors
    {
    returnval = -1;
    } if(!CirBufNotEmpty())    // check for no response
    {
    returnval = -1;
    } if(!returnval)
    {
    if(GetCirBuf() != NULL)
        {returnval = -1;} if(GetCirBuf() != 'D')
        {returnval = -1;}
    }
return(returnval);

} // end of DownLoad

//*******************************************************************
// Start Run loop: gets the run loop going
// Calling program must verify that download was successful
void StartRunLoop(void)
{
CloseSerial();   // unload the buffered serial communications IRQ
OpenSerialRunTime(NumRegions); // load runtime IRQ
outCOM1('R');        // put into run mode
}

//*******************************************************************
// Stop Run loop: terminates run mode
```

```c
void StopRunLoop(void)
{
outCOM1('S');    // send a stop command
delay(250);      //wait 250ms for remote to respond
CloseSerial();   // unload the buffered serial communications IRQ
OpenSerialBuffered();
ClearCirBuf();
}

//*********************************************************************
// Running loop:  this code is executed whenever the conduvtivity meter
// is in run mode.
RunLoop(void)
{
PlotCSA(DisplayData,Lookup);
}

//*********************************************************************
// Calibrate loop:  this code is executed to perform a calibrate cycle.
CalLoop(void)
{
}

//*********************************************************************
// Wait loop: this code is executed while setup opperations are being
// performed.  It continuously checks for the presence of the conductivity
// meter and when found it loads the sensor and calibration file for the
// probe attached.

WaitLoop(void)
{
int i,comm;
char c;

c = sensorcode;
comm = GetRemoteState();   // read the remote state and sensor code
if(comm && c != sensorcode) // check if sensor has changed
   {
   if(sensorcode == 63)
      { // no sensor connected
      ShowStatus("SENSOR CABLE DISCONNECTED!!");
      }
   else
      { // sensor is connected
      CfgOK = LoadConfigFile(sensorcode);
      switch(CfgOK)
         {
         case 1:
            if(DownLoad() == 0) // download configuration
               {
               ShowStatus("Successfully Loaded sensor configuration");
               }
            else
               {
               ShowStatus("config file OK but DOWNLOAD FAILED!!");
               }
            break;

case -1:
```

```
                ShowStatus("CONFIGURATION FILE NOT FOUND!!");
                break;

case -2:
                ShowStatus("CONFIG FILE VERSION ERROR!!");
                break;
            }
        }
    }
if(comm == 0)
    {
    ShowStatus("COMMUNICATION FAILURE!!");
    }
} // end of WaitLoop //*********************************************************************
//*********************************************************************
//*********************************************************************
//********************************************************************* define MENU1    "Run  Stop  Cal  Quit"

void main(void)
{
int i;
int error = 0;
char c;

clrscr();
printf("CONDUCTIVITY METER DISPLAY\n");
printf("%s\n\n",copywrite);

error = BootRemote();   // start up serial port and establish communications if(!error)
    {
    ShowVersion();
    VGAgraphics();          // put into mode 13 VGA
    setpalette();           // create pallete
    MenuLine(MENU1);        // display menu line for(i=16;i!=256;i++)
        {
        PutPixel(i-15,20,i);
        PutPixel(i-1o,21,i);
        PutPixel(i-16,22,i);
        } while(!error && SystemState != QUIT)
        {
        switch(SystemState)
            {
            case WAIT:
                WaitLoop();
                if(AnyButton())
                    {
                    DownLoad();
                    SystemState = QUIT;
```

```
            }
        break;

case CAL:
        CalLoop();
        break;

case INT:
        break;

case RUN:
        RunLoop();
        break;

default:
        break;
    }
if(kbhit()) // check for any key hit
    {
    switch(getch())
        {
        case 'r':
        case 'R':
            if(CfgOK)
                {
                // temp
                DisplayData[0] = 50;
                DisplayData[1] = 60;
                DisplayData[2] = 70;
                DisplayData[3] = 80;

if(RemoteState == CFG) //check that remote is configured
                    {
                    SystemState = RUN;
                    ShowStatus("System Running");
                    }
                else
                    {
                    ShowStatus("Unable to run, remote not configued");
                    }
                }
            else
                {ShowStatus("Unable to run, no calibration");}
            break;

case 's':
        case 'S':
            {
            if(SystemState == RUN)
                {
                SystemState = WAIT;
                ShowStatus("System Stopped");
                }
            }
            break;

case 'c':
        case 'C':
            break:
```

```
            case 'q':
            case 'Q':
                ShowStatus("QUIT: are you sure Y/N");
                c = getch();
                if(c=='y' || c == 'Y')
                    {SystemState = QUIT;}
                ShowStatus("");
                break;

default:
                MenuLine(MENU1);
                ShowStatus("");
                break;
            }
        }
    }
    VGAText();      // return to text mode
    }
CloseSerial(); // turn off serial port
fatalerror(error);
} // end of main /*
main()
{
int i;
clrscr();
printf("Creating Screen Graphics Layouts.....\n");
CreateScreenLookup13(150,100);
gotoxy(1,11);
InitData();
GoMouse();
for(i=0;i!=256;i++)
    {
    PutPixel(i,4,(char)i);
    PutPixel(i,5,(char)i);
    PutPixel(i,6,(char)i);
    }
for(i=0;!kbhit();i++)
    {
    PlotCSA(DisplayData,Lookup);
    }
getch();
gotoxy(5,5);
printf("%d cycles completed",i);

DisplaySensor();
ShowCursor();
while(!kbhit())
    {;}
HideCursor();

} // end of main
```

```
 */

//*********************************************************************
//***************************************************************** void EraseCfg(void)
{
int i;

LengthLookup = 0;
NumRegions = 0;

for(i=0;i!=VID_TABLE;i++)
    {Lookup[i]=0;}
for(i=0;i!=ELECT_PAIR;i++)
    {
    Electrodes[i][1] = 0;
    Electrodes[i][2] = 0;
    }
} // end of EraseCfg

//******************************************************************
```

```cpp
// CREATE.CPP
// Last revised 3/20/93
// This is an editor for creating the configuration files used by
// the conductivity analyzer.  The config files contian video maps and
// electrode pair information.

#include <stdio.h>
#include <stdlib.h>
#include <alloc.h>
#include <dos.h>
#include <conio.h>
include <math.h> int GetMouseX(void);   // function prototypes
int GetMouseY(void);
int AnyButton(void);
void HideCursor(void);
void ShowCursor(void);
int VGAgraphics(void);
void VGAText(void);

// global variables
// MAKE SURE PALLETTE BUFFER IS DECLARED FIRST
char pal[256*3];  // create memory array for my palette char copywrite[32] = {"COPYRIGHT 1993 JULIAN WARHURST\0"};

define  VID_TABLE    5000
#define  ELECT_PAIR   70
define  MAX_ELECT    32 struct coord{
           int x;
           int y;
           };
struct coord nodes[13]; // screen locations of the electrodes
char DisplayData[31];
struct coord mid[18];
int LengthLookup = 0;
int Lookup[VID_TABLE+1];
int NumRegions = 0;
char Electrodes[ELECT_PAIR+1][2];
int RedrawMenu = 1;
char FileName[13] = {"SENSORxx.CFG\0"};
FILE *sensorfile;

#define circleX   160
#define circleY   100
#define Xmult     1.15
#define maxrad    60
int radius = 5;

int CurrentRegion =-1; // note region 0 is first region

//*****************************************************************

// General purpose mouse utilities used for user interface
```

```c
#define MOUSE 0x33
union REGS iReg,oReg;
struct SREGS segregs;

//*********************************************************************
/* GoMouse attemts to turn on the mouse driver and will return an error
   if a mouse or driver is not found */

GoMouse(void)
{ iReg.x.ax = 0;
int86(MOUSE, &iReg, &oReg);
if(oReg.x.ax == -1)
    {return(0);}
else
    {return(-200);}
}  // end of GoMouse

//*********************************************************************

/* ShowCursor make the mouse cursor visible on the screen */ void ShowCursor(void)
{
iReg.x.ax = 1;
int86(MOUSE, &iReg, &oReg);
}  // end of ShowCursor

//*********************************************************************

/* Hide cursor turns the mouse cursor off */ void HideCursor(void)
{
iReg.x.ax = 2;
int86(MOUSE, &iReg, &oReg);
}  // end of HideCursor

//*********************************************************************

/* detects if any mouse buttons are pushed */ int AnyButton(void)
{
iReg.x.ax = 3;
int86(MOUSE, &iReg, &oReg);
return(oReg.x.bx);
}

//********************************************************************* int GetMouseX(void)
{
iReg.x.ax = 3;
int86(MOUSE, &iReg, &oReg);
return((oReg.x.cx)/2); // note divided by 2 for this VGA mode only
} // end of GetMouseX
```

```c
//*****************************************************************
int GetMouseY(void)
{
int i;
iReg.x.ax = 3;
int86(MOUSE, &iReg, &oReg);
i=(oReg.x.dx)-1; // -1 prevents the need to hide mouse when writing pixel
if(i<1)
    {i=1;}
return(i);
} // end of GetMouseY

//***************************************************************** char GetCtrlKeys(void)
{
char c;
/*   BIT         SIGNIFICANCE
     0              right shift
     1              left shift
     2              ctrl key
     3              alt key
     4              scroll lock on
     5              num lock on
     6              caps lock on
     7              insert on
*/
asm    {  // call bios to read control keys
        mov   ah,02h
        int   16h
        mov   c,al
        }
return(c);
} // end of GetCtrlKeys //*****************************************************************
// THIS FUNCTION SET THE DISPLAY CARD INTO MODE 13
// CALLED AS    VGAgraphics();

int VGAgraphics()
{
int returnval = 0;
asm   {
        mov   ax,0013h  /* call interrupt 10 setting to mode 13 */
        /* note this is really sending command 00 (set graphics mode)
           followed by command 13 (mode 13) */
        int   10h
        }
return(returnval);
} // end of VGAgraphics()

//*****************************************************************
//; THIS FUNCTION SETS THE DISPLAY CARD INTO TEXT MODE
//; CALLED AS    VGAText();

void VGAText()
{
asm    {
```

```
        mov    ax,1200h
        mov    bx,0031h
        int    10h
        mov    ax,0003h
        /* sets back to mode 3   which is 80 x 25 16 color CGA*/
        int    10h
        }
} // end of VGAText()

//*****************************************************************
// THIS FUNCTION PUTS A PIXEL OF A SPECIFIC COLOR AT LOCATION X,Y void PutPixel(int x,int y,char color)
{
unsigned int i;
char far *s;
i = (320 * y) + x;
s = (char*)MK_FP(0xa000,0);
s[i] = color;
} // end of put pixel //*****************************************************************
// THIS FUNCTION GETS A PIXEL LOCATION X,Y char GetPixel(int x,int y)
{
unsigned int i;
char far *s;
i = (320 * y) + x;
s = (char*)MK_FP(0xa000,0);
return(s[i]);
} // end of GetPixel //*****************************************************************
// THIS FUNCTION CLEARS THE SCREEN void ClearScreen(void)
{
unsigned int i;
char far *s;
s = (char*)MK_FP(0xa000,0);
for(i=0;i != (320*200);i++)
    {
    s[i] = BLACK;
    }
} // end of ClearScreen()

//***************************************************************** void EraseCfg(void)
{
int i;

LengthLookup = 0;
NumRegions = 0;

for(i=0;i!=VID_TABLE;i++)
    {Lookup[i]=0;}
```

```c
for(i=0;i!=ELECT_PAIR;i++)
    {
    Electrodes[i][1] = 0;
    Electrodes[i][2] = 0;
    }
} // end of EraseCfg

//***************************************************************** void cir(int X,int Y, int R, char color)
{ // circle utility for this graphics mode
int i,x,y;
for(i=0;i!=(2*R);i++) // i is the Y coord
    {
    x = (int)((float)R*Xmult*cos(3.1415926*i/(4*R)));
    y = (int)((float)R*sin(3.1415926*i/(4*R)));
    PutPixel(X+x,Y+y,color);
    PutPixel(X-x,Y+y,color);
    PutPixel(X+x,Y-y,color);
    PutPixel(X-x,Y-y,color);
    }
} // end of cir

//***************************************************************** void DoMessage(char message[])
 // clears and reprints the message sent in in message window
{
HideCursor(); // turn mouse off
gotoxy(1,2);
printf("                                                    ");
gotoxy(1,2);
printf("%s",message);
ShowCursor(); // turn mouse back on
} // end of DoMessage

//***************************************************************** void DoCircle(void)
 /* draws a circle as defined by the mouse
   */
{
unsigned int x,y;
int oldradius;
int lx = 0;
int ly = 0;

oldradius = radius;
HideCursor(); // turn mouse off
DoMessage("DRAG CIRCLE WITH MOUSE");
ShowCursor(); // turn mouse back on
while(AnyButton() != 0)
    {;} // wait for mouse release
while(AnyButton() != 1 && !kbhit())
    {;} // wait for first mouse button
while(AnyButton() == 1 && !kbhit())
    {
    x = GetMouseX();
    y = GetMouseY();
    if(x != lx || y != ly)
```

```c
    { // if mouse moved then redraw circle
    HideCursor(); // turn mouse off
    cir(circleX,circleY,radius,BLACK); // erase old circle
    lx = x; // update mouse position
    ly = y;
    x = x - circleX;
    y = y - circleY;
    radius = (int)(sqrt((x*x)/Xmult+(y*y)));
    if(radius>maxrad)
        {radius = maxrad;}
    cir(circleX,circleY,radius,WHITE); // draw new circle
    ShowCursor(); // turn mouse back on
    }
    }
if(kbhit())
    {
    getch(); // flush the key
    cir(circleX,circleY,radius,BLACK); // erase old circle
    radius = oldradius;
    cir(circleX,circleY,radius,WHITE); // draw new circle
    }
else
    { // since radius changed, erase screen lookup table
    EraseCfg();
    ClearScreen();
    }
RedrawMenu = 1;
} // end of DoCircle /*****************************************************************
 *  This function creates a VGA pallet consisting of a 16 - 255 which
 *  is a color scale designed to offer contrast, not scale
 */ void setpalette()
{
int i,j;

//BLACK          0
//BLUE           1
    pal[(1*3)+2] = 63;
//GREEN          2
    pal[(2*3)+1] = 63;
//CYAN           3
    pal[(3*3)+1] = 63;
    pal[(3*3)+2] = 63;
//RED            4
    pal[(4*3)+0] = 63;
//MAGENTA        5
    pal[(5*3)+0] = 63;
    pal[(5*3)+2] = 63;
//BROWN          6
    pal[(6*3)+0] = 63;
    pal[(6*3)+1] = 32;
    pal[(6*3)+2] = 32;
//LIGHTGRAY      7
    pal[(7*3)+0] = 32;
    pal[(7*3)+1] = 32;
    pal[(7*3)+2] = 32;
```

```
//DARKGRAY        8
   pal[(8*3)+0]  = 16;
   pal[(8*3)+1]  = 16;
   pal[(8*3)+2]  = 16;
//LIGHTBLUE       9
   pal[(9*3)+2]  = 32;
//LIGHTGREEN     10
   pal[(10*3)+1] = 32;
//LIGHTCYAN      11
   pal[(11*3)+1] = 32;
   pal[(11*3)+2] = 32;
//LIGHTRED       12
   pal[(12*3)+0] = 32;
//LIGHTMAGENTA   13
   pal[(13*3)+0] = 32;
   pal[(13*3)+2] = 32;
//YELLOW 14
   pal[(14*3)+0] = 63;
   pal[(14*3)+1] = 63;
//WHITE 15
   pal[(15*3)+0] = 63;
   pal[(15*3)+1] = 63;
   pal[(15*3)+2] = 63;

// contrast pallette from 16-156 for(i=0;i!=7;i++)  // 7 basic colors
   {
   for(j=0;j!=10;j++)  // 10 shades/color
      {
      if(i==0||i==2||i==4||i==6)
         {pal[3*((i*10)+j)+48]      = j*4+27;}  // red if(i==1||i==2||i==5||i==6)
         {pal[3*((i*10)+j)+49]      = j*4+27;}  // green if(i>2)
         {pal[3*((i*10)+j)+50]      = j*4+27;}  // blue
      }
   } asm   {
      mov   ax,ds
      mov   es,ax
      mov   ax,1012h
      mov   bx,0000h
      mov   cx,256
      mov   dx,offset pal
      int   10h
      }
} // end of setpalette

//***************************************************************** int GetSensorFile(void)
{
int i,done;
int returnval = 0;
```

```
char onechar,code[2],version[20];

i = 0;
done = 0;
while(!done)
    {
    onechar = getch();
    if(onechar == 8 && i!=0) // check for Backspace
        {
        putch(8);    // backup
        putch(' ');  // output a space
        putch(8);    // backup again
        i--;
        }
    if(onechar == 13 && i==2) // check for <CR>
        {done++;}
    if(onechar >= '0' && onechar <= '9' && (i != 2))
        {
        code[i] = onechar;
        putch(onechar);
        i++;
        }
    if(onechar == 27) // check for ESC
        {
        done++;
        returnval = -1;
        }
    }
if(!returnval)
    {
    FileName[6] = code[0];
    FileName[7] = code[1];
    // check if file exists already
    sensorfile = fopen(FileName,"rb");
    if(sensorfile) // file already exists!
        {
        // load all the variables fseek(sensorfile,0,SEEK_SET); // first get version information
        fread(version,20,1,sensorfile);

// detect the version number in the version string
        switch(version[8])
            {
            case '1':
                fseek(sensorfile,0,SEEK_CUR); // then get circle radius
                fread(&radius,sizeof(radius),1,sensorfile);

fseek(sensorfile,0,SEEK_CUR); // then get Length of lookup table
                fread(&LengthLookup,sizeof(LengthLookup),1,sensorfile);

fseek(sensorfile,0,SEEK_CUR); // then get the number of regions
                fread(&NumRegions,sizeof(NumRegions),1,sensorfile);

fseek(sensorfile,0,SEEK_CUR); // Now read in electrode table
                fread(Electrodes,ELECT_PAIR*2,1,sensorfile); // read the lookup tabl fseek(sensorfile,0,SEEK_CUR); // Now read in the screen lookup table
                fread(Lookup,LengthLookup*sizeof(LengthLookup),1,sensorfile);
```

```
                if(NumRegions) // check if any regions defined)
                    {CurrentRegion=0;}
                else
                    {CurrentRegion=-1;}
                break;

default:
                DoMessage("UNKNOWN SENSOR FILE VERSION");
                delay(1000);
                break;
            }
        fclose(sensorfile);

}
    }
return(returnval);
} // end of GetSensorFile

//***************************************************************** int SaveSensorFile(void)
{
int returnval = 0;
char version[20] = {"sensor V1.0"};
if(sensorfile = fopen(FileName,"wb"))
    {
    fseek(sensorfile,0,SEEK_SET); // first write version string
    fwrite(version,20,1,sensorfile);

fseek(sensorfile,0,SEEK_CUR); // then write circle radius
    fwrite(&radius,sizeof(radius),1,sensorfile);

fseek(sensorfile,0,SEEK_CUR); // then write Length of lookup table
    fwrite(&LengthLookup,sizeof(LengthLookup),1,sensorfile);

fseek(sensorfile,0,SEEK_CUR); // then write Number of regions
    fwrite(&NumRegions,sizeof(NumRegions),1,sensorfile);

fseek(sensorfile,0,SEEK_CUR); // Now write out the electrode table
    fwrite(Electrodes,ELECT_PAIR*2,1,sensorfile); // read the lookup table fseek(sensorfile,0,SEEK_CUR); // Now write out the screen lookup table
    fwrite(Lookup,LengthLookup*sizeof(LengthLookup),1,sensorfile);

returnval = fclose(sensorfile);
    }
else
    {returnval = -1;} // error opening file return(returnval);
} // end of SaveSensorFile

//***************************************************************** int DoMenu(void)
 /* note uses global variable RedrawMenu
  * returns a code for each menu item
  *      0 = no mouse pushed, or undefined combination
  *      1 = Left mouse button outside of menu area
  *      2 = Right mouse button outside of menu area
```

```
*        4 = Center mouse button
*       50 = Circle selected
*       60 = Region selected
*       70 = Save selected
*       80 = Exit selected
*/
{
int Returnval,ButtonCode,X;
unsigned int i;
char far *s;
if(RedrawMenu)
    {
    RedrawMenu = 0; // clear redraw flag
    HideCursor(); // turn off mouse // clear menu and message areas
    s = (char*)MK_FP(0xa000,0);
    for(i=0;i != (320*35);i++)
        {
        s[i] = BLACK;
        }
    gotoxy(1,1);
    printf("CIRCLE   REGION   READ   SAVE   EXIT");

cir(circleX,circleY,radius,WHITE);
    if(CurrentRegion == -1)
        {
        gotoxy(1,24);
        printf("No regions defined");
        }
    else
        {
        gotoxy(1,24);
        printf("                    "); // clear the region display
        gotoxy(1,24);
        printf("REG= %d",CurrentRegion);
        }
    ShowCursor(); // turn mouse back on
    }
if(ButtonCode = AnyButton())
    {
    if(GetMouseY() > 8)
        { // not in menu region
        Returnval = ButtonCode;
        }
    else
        { // in menu region
        X = GetMouseX();
        if(X<6*8)
            {Returnval = 50;} // circle selected
        if(X>9*8 && X<15*8)
            {Returnval = 60;} // region selected
        if(X>18*8 && X<22*8)
            {Returnval = 70;} // read selected
        if(X>25*8 && X<29*8)
            {Returnval = 80;} // save selected
        if(X>32*8 && X<36*8)
            {Returnval = 90;} // exit selected
        }
    }
```

```
return(Returnval);
} // end of DoMenu

//*******************************************************************
// min is minimum allowed
// max is maxumum allowed
// default is number to return if just <CR>, if default = -1 then
// a default IS NOT ALLOWED.

int InputInt(int min,int max,int DefaultInt)
{
int i,j;
char code[6],onechar;
int done=0;
while(!done)
    {
    onechar = getch();
    if(onechar == 8 && i!=0) // check for Backspace
        {
        printf("%c",8) ;   // backup
        printf(" ")    ;   // output a space
        printf("%c",8) ;   // backup again
        i--;
        code[i] = NULL;
        }
    if(onechar == 13 && i>0 ) // check for <CR>
        {
        j = atoi(code);
        if(j <= max && j >= min)
            {done++;}
        }
    if(onechar == 13 && i==0 && DefaultInt!=-1)  // default mechinism
        {
        j = DefaultInt; // return the default value
        done++;
        }
    if(onechar >= '0' && onechar <= '9' && (i != 4))
        {
        code[i] = onechar;
        printf("%c",onechar);
        i++;
        code[i] = NULL;
        }
    }
return(j);

} // end of InputIn

//******************************************************************* void DoEraseAllRegion(int Region)
{
unsigned int i;
char far *s;
CurrentRegion = -1;
NumRegions = 0;
HideCursor(); // turn off mouse
s = (char*)MK_FP(0xa000,0);
for(i=0;i != (320*200);i++)
    {
```

```
        if(s[i] == Region+16)
            {s[i] = BLACK;}
        }
ShowCursor();
} // end of DoEraseAllRegion

//********************************************************************* void DoRegion(void)
  // selects the region to modify

{
int OK = 0;
char a,b;
int i,j,k,DefaultInt,MaxNoRegions;

if(NumRegions == ELECT_PAIR-1)  // limits the numer of regions
    {
    MaxNoRegions = ELECT_PAIR-1;
    }
else
    {
    MaxNoRegions = NumRegions;
    }

DoMessage("ENTER REGION # : ");
CurrentRegion = InputInt(0,MaxNoRegions,-1); // must define regions in order
if(CurrentRegion == NumRegions) // check if this is a new region
    {NumRegions++;}          // if new region, increaase the number of regions while(!OK)
    {
    DoMessage("FIRST ELECTRODE # (0 clears) : ");
    a = Electrodes[CurrentRegion][0];
    DefaultInt = -1;
    if(a != 0)
        {
        printf("[%d] ",(int)a);
        DefaultInt = (int)a;
        }
    Electrodes[CurrentRegion][0] = InputInt(0,MAX_ELECT,DefaultInt);
    if(a && !Electrodes[CurrentRegion][0])
        {
        gotoxy(1,2);
        printf("Regions %d to %d removed",CurrentRegion,NumRegions-1);
        for(i=CurrentRegion;i>NumRegions;i++
            {
            DoEraseAllRegion(i);
            Electrodes[i][0] = 0;
            Electrodes[i][1] = 0;
            }
        if(CurrentRegion > -1) // check if any regions at all
            {CurrentRegion--;}
        NumRegions = CurrentRegion+1;
        OK++;
        }
    else
        {
        DoMessage("SECOND ELECTRODE # : ");
        b = Electrodes[CurrentRegion][1];
```

```
        DefaultInt = -1;
        if(b != 0)
            {
            printf("[%d] ",(int)b);
            DefaultInt = (int)b;
            }
        Electrodes[CurrentRegion][1] = InputInt(1,MAX_ELECT,DefaultInt);
        // check if electrodes are the same
        if(Electrodes[CurrentRegion][0] != Electrodes[CurrentRegion][1])
            {
            OK++;
            }
        }
    }
RedrawMenu = 1;
} // end of DoRegion

//***************************************************************** int InCircle(int X, int Y)
{
unsigned int r,dx,dy;
int returnval = 0;

dx = circleX-X; // get vector differences
dy = circleY-Y;
r = (int)sqrt((float)(dx*dx)/(Xmult*1.1)+(float)(dy*dy));
if(r < radius)
    {
    returnval = 1;
    }
return(returnval);
}

//***************************************************************** void DoWriteRegion(void)
{
int x,y,x0,y0;

x0 = GetMouseX(); // initial click location
y0 = GetMouseY();
while(AnyButton() == 1)
    {
    x = GetMouseX();
    y = GetMouseY();
    if(GetCtrlKeys(,&3) // check if a shift key is pressed
        {
        if(abs(x-x0) > abs(y-y0))
            {y = y0;}    // draws horizontal line
        if(abs(y-y0) > abs(x-x0))
            {x = x0;}    // draws vertical line
        }
    // verify that in circle, pixel not used by other region and mouse not moved
    if(InCircle(x,y) && GetPixel(x,y) == BLACK && x==GetMouseX() && y==GetMouseY(
        {
        PutPixel(x,y,(char)(CurrentRegion+16));
        }
    }
} // end of DoWriteRegion
```

```c
//****************************************************************** void HorizLine(int Y,int FromX,int ToX, char color)
{
int i;
for(i=FromX;i<ToX;i++)
   {PutPixel(i,Y,color);}
} // end of HorizLine

//****************************************************************** int FindFirstLeft(int Y,char color)
{
char far *s;
int i,j;

s = (char*)MK_FP(0xa000,0);
j = -1;
for(i=319;i!=0;i--)
    {
    if(s[(unsigned)(i+(320*Y))] == color)
        {
        j = i; //  latch in left most
        }
    }
return(j);
} // end of FindFirstLeft

//****************************************************************** int FindFirstRight(int Y,char color)
{
char far *s;
int i,j;

s = (char*)MK_FP(0xa000,0);
j = -1;
for(i=0;i!=320;i++)
    {
    if(s[(unsigned)(i+(320*Y))] == color)
        {
        j = i; //  latch in right most
        }
    }
return(j);
} // end of FindFirstRight

//****************************************************************** void DoFillRegion(void)
{
int xl,xr,yi;

HideCursor();
for(yi=20;yi!=200;yi++)
    {
    xl = FindFirstLeft(yi,CurrentRegion+16);
    xr = FindFirstRight(yi,CurrentRegion+16);
    if(xl != -1)
```

```
            {
            HorizLine(yi,xl,xr,CurrentRegion+16);
            }
        }
ShowCursor();
} // end of DoFillRegion

//********************************************************************* void DoEraseRegion(void)
{
int x,y;
x = GetMouseX();
y = GetMouseY();
if(InCircle(x,y) && GetPixel(x,y) != BLACK)
    {
    HideCursor();
    PutPixel(x,y,BLACK);
    ShowCursor();
    }
} // end of DoEraseRegion //*********************************************************************
// Function plots the provided display data acording to the provided
// screen draw lookup table.
// The data is a list of values to be plotted.  The length is variable,
// terminated by 0.
// For every data point, the lookup table describes a region to fill
// with that value (color).  The lookup table consists of pairs of integers:
//              Starting address
//              Ending address
//              Starting address
//              Ending address
//              NULL
//              Starting address
//                  :       :
// A null starting address indicates that that region is complete.

void ReadLookup()
{
int i,j;
register unsigned int index,endindex;
register char far *s;
register char color;
s = (char*)MK_FP(0xa000,0);

j = 0; // lookup table pointer
color = 16; // color counter
while(j < LengthLookup)
    {
    while(Lookup[j]) // check for non-null starting value
        {
        index = Lookup[j++];
        endindex = Lookup[j++];
        while(index++ != endindex)
            {
            s[index] = color; // write pixels out
            }
```

```
        }
    j++;  // get past the null
    color++;  // increment color value
    }
}  // end of ReadLookup //*****************************************************************
// Function converts the screen image within the circle to a lookup
// table to be used at run time.
// For every data point, the lookup table describes a region to fill
// with that value (color).  The lookup table consists of pairs of integers:
//          Starting address
//          Ending address
//          Starting address
//          Ending address
//          NULL
//          Starting address
//              :        :
// A null starting address indicates that that region is complete.

void MakeLookup()
{
unsigned int i,j,k;
int inzone;
char far *s;
s = (char*)MK_FP(0xa000,0);

LengthLookup = 0;
for(i=0;i <= NumRegions;i++) // scan all current regions
    {
    inzone = 0;
    for(j=(320*(circleY-maxrad-1));j != (320*200);j++)
        {
        if(inzone)
            {
            if(s[j] != i+16) // check if still in zone
                {
                inzone = 0;    // remember left the zone
                Lookup[LengthLookup] = j; // make note that left
                LengthLookup++;
                }
            }
        else if(s[j] == i+16) // check if entering zone
                {
                inzone = 1;    // remember entered the zone
                Lookup[LengthLookup] = j; // make note that entered
                LengthLookup++;
                }

}
    Lookup[LengthLookup] = 0; // mark end of region
    LengthLookup++;
    }
Lookup[LengthLookup] = 0; // mark end of list with second NULL
LengthLookup++;

}  // end of MakeLookup

//*****************************************************************
```

```c
void ReadRegion(void)
{
int c;
while(AnyButton()) {;} // wait for mouse release
while(!AnyButton()) {;} // wait for new click
HideCursor();
c = (int)(GetPixel(GetMouseX(),GetMouseY()))-16;
gotoxy(1,25);
printf("                    ");
if(c>=0)
   {
   gotoxy(1,25);
   printf("THIS IS REGION %d",c);
   }
else
   {
   gotoxy(1,25);
   printf("THIS IS NOT A REGION");
   }
ShowCursor(); // turn mouse back on
while(AnyButton()) {;} // wait for mouse release
} // end of DoEraseAllRegion

//***************************************************************** void main()
{
int i,error;
int done = 0;
clrscr();
printf("CREATE UTILITY\n");
printf("%s\n\n\n",copywrite);
EraseCfg();

printf("What is the code number of the sensor are you configuring?");
error = GetSensorFile(); // load u; sensor file if present
clrscr();
if(!error) {error=GoMouse();}
if(!error) {error=VGAgraphics();}
if(!error)
    {
    setpalette();
    ReadLookup();
    ShowCursor();
    while(!done)
        {
        switch(DoMenu())
            { case 1:
               DoWriteRegion();
               break;

case 2:
               DoEraseRegion();
               break;

case 4:
               DoFillRegion();
```

```
                break;

case 6:
                DoEraseAllRegion(CurrentRegion);
                break;

case 50:        // circle selected
                DoCircle();
                break;

case 60:        // region selected
                DoRegion();
                break;

case 70:        // read selected
                ReadRegion();
                break;

case 80:        // save selected
                DoMessage("CREATING LOOKUP TABLE");
                MakeLookup();
                DoMessage("SAVING SENSOR FILE");
                SaveSensorFile();
                DoMessage("");
                break;

case 90:        // exit selected
                done = 1;
                break;

default:
                break;
            }
        }
    VGAText();
    }
if(error)
    {printf("ERROR CODE %d!",error);}
} // end of main
```

```cpp
// SCREEN.CPP  generic 256 color graphics mode,
// mouse driven menu video driver
// provides all screen graphics functions and menus for CONDUCT
// last revised 3/28/93 include <stdio.h>
include <alloc.h>
#include <dos.h>
#include <conio.h>
include <math.h> int GetMouseX(void);    // function prototypes
int GetMouseY(void);
int AnyButton(void);
void HideCursor(void);
void ShowCursor(void);
void VGAgraphics(void);
void VGAText(void);

// global variables
// MAKE SURE PALLETTE BUFFER IS DECLARED FIRST
char pal[256*3];   // create memory array for my palette struct coord{
            int x;
            int y;
            };
struct coord nodes[13]; // screen locations of the electrodes

//*****************************************************************

// General purpose mouse utilities used for user interface define MOUSE 0x33
union REGS iReg,oReg;
struct SREGS segregs;

//*****************************************************************
/* GoMouse attemts to turn on the mouse driver and will return an error
   if a mouse or driver is not found */

GoMouse(void)
{ iReg.x.ax = 0;
int86(MOUSE, &iReg, &oReg);
if(oReg.x.ax == -1)
   {return(0);}
else
   {return(-200);}
}  // end of GoMouse

//***********************************************************

/* ShowCursor make the mouse cursor visible on the scree void ShowCursor(void)
{
iReg.x.ax = 1;
```

```c
int86(MOUSE, &iReg, &oReg);
}  // end of ShowCursor

//*****************************************************************

/* Hide cursor turns the mouse cursor off */ void HideCursor(void)
{
iReg.x.ax = 2;
int86(MOUSE, &iReg, &oReg);

}  // end of HideCursor

//*****************************************************************

/* detects if any mouse buttons are pushed */

AnyButton(void)
{
iReg.x.ax = 3;
int86(MOUSE, &iReg, &oReg);
return(oReg.x.bx);
}

//***************************************************************** int GetMouseX(void)
{
iReg.x.ax = 3;
int86(MOUSE, &iReg, &oReg);
return(oReg.x.cx);
}  // end of GetMouseX

//***************************************************************** int GetMouseY(void)
{
iReg.x.ax = 3;
int86(MOUSE, &iReg, &oReg);
return(oReg.x.dx);
}  // end of GetMouseY //*****************************************************************
// THIS FUNCTION SET THE DISPLAY CARD INTO MODE 13
// CALLED AS     VGAgraphics();

void VGAgraphics()
{
asm    {
       mov   ax,0013h  /* call interrupt 10 setting to mode
       /* note this is really sending command 00 (set grar
          followed by command 13 (mode 13) */
       int   10h
       }
}  // end of VGAgraphics()

//*************************************************
//; THIS FUNCTION SETS THE DISPLAY CARD INTO TEXT MODE
//; CALLED AS    VGAText();
```

```c
void VGAText()
{
asm     {
        mov     ax,1200h
        mov     bx,0031h
        int     10h mov     ax,0003h
        /* sets back to mode 3   which is 80 x 25 16 color CGA*/
        int     10h
        }
} // end of VGAText()

//*****************************************************************
// THIS FUNCTION PUTS A PIXEL OF A SPECIFIC COLOR AT LOCATION X,Y void PutPixel(int x,int y,char color)
{
unsigned int i;
char far *s;
i = (320 * y) + x;
s = (char*)MK_FP(0xa000,0);
s[i] = color;
} // end of put pixel //*****************************************************************
// THIS FUNCTION BLANKS THE LINE AT A SPECIFIED Y ADDRESS void BlankLine(int y)
{
unsigned int i,start,end;
char far *s;
start = y*320*8;
end   = start+(320*8);
s = (char*)MK_FP(0xa000,0);
for(i=start;i!=end;i++)
    {
    s[i] = 0;
    }
} // end of BlankLine //*****************************************************************
// THIS FUNCTION CLEARS THE SCREEN void ClearScreen(void)
{
unsigned int i;
char far *s;
s = (char*)MK_FP(0xa000,0);
for(i=0;i != (320*200);i++)
    {
    s[i] = 0;
    }
} // end of ClearScreen()

/*****************************************************************
 * This function creates a VGA pallet consisting of a 0 - 247 which
 * is a progressive color scale for contour display.
 * in addition there are 8 reserved colors listed below.
```

```
*/
//#define MyBlack   248
//#define MyRed     249
//#define MyBlue    250
//#define MyGreen   251
//#define MyMagenta 252
//#define MyCyan    253
//#define MyYellow  254
//#define MyWhite 255 void setpalette(void)
{
int i;

//BLACK          0
   pal[0] = 0; // set backg(int) color palette entry 0
   pal[1] = 0;
   pal[2] = 0;
//BLUE           1
   pal[(1*3)+2] = 63;
//GREEN          2
   pal[(2*3)+1] = 63;
//CYAN           3
   pal[(3*3)+1] = 63;
   pal[(3*3)+2] = 63;
//RED            4
   pal[(4*3)+0] = 63;
//MAGENTA        5
   pal[(5*3)+0] = 63;
   pal[(5*3)+2] = 63;
//BROWN          6
   pal[(6*3)+0] = 63;
   pal[(6*3)+1] = 32;
   pal[(6*3)+2] = 32;
//LIGHTGRAY      7
   pal[(7*3)+0] = 32;
   pal[(7*3)+1] = 32;
   pal[(7*3)+2] = 32;
//DARKGRAY       8
   pal[(8*3)+0] = 16;
   pal[(8*3)+1] = 16;
   pal[(8*3)+2] = 16;
//LIGHTBLUE      9
   pal[(9*3)+2] = 32;
//LIGHTGREEN    10
   pal[(10*3)+1] = 32;
//LIGHTCYAN     11
   pal[(11*3)+1] = 32;
   pal[(11*3)+2] = 32;
//LIGHTRED      12
   pal[(12*3)+0] = 32;
//LIGHTMAGENTA  13
   pal[(13*3)+0] = 32;
   pal[(13*3)+2] = 32;
//YELLOW 14
   pal[(14*3)+0] = 63;
   pal[(14*3)+1] = 63;
//WHITE 15
   pal[(15*3)+0] = 63;
```

```
    pal[(15*3)+1] = 63;
    pal[(15*3)+2] = 63;

// 16 reserved black
// 255 reserved white
// color scale pallette from 16-255

//BLACK 16
    pal[(16*3)+0] = 0;
    pal[(16*3)+1] = 0;
    pal[(16*3)+2] = 0;

// fade from dark blue to dark cyan
for(i=17;i!=48;i++)
    {
    pal[(i*3)]   = 0;           // red
    pal[(i*3)+1] = (char)i-16;  // green
    pal[(i*3)+2] = 32;          // blue
    }
// now fade from dark cyan to bright cyan
for(i=48;i!=80;i++)
    {
    pal[(i*3)]   = 0;           // red
    pal[(i*3)+1] = (char)i-16;  // green
    pal[(i*3)+2] = (char)i-16;  // blue
    }
// now fade to green
for(i=80;i!=124;i++)
    {
    pal[(i*3)]   = 0;           // red
    pal[(i*3)+1] = 63;          // green
    pal[(i*3)+2] = (char)(143-i); // blue
    }
// and continue fade to yellow
for(i=124;i!=172;i++)
    {
    pal[(i*3)]   = (char)(i-108);  // red
    pal[(i*3)+1] = 63;          // green
    pal[(i*3)+2] = 0;           // blue
    }
// now fade to red
for(i=172;i!=236;i++)
    {
    pal[(i*3)]   = 63;          // red
    pal[(i*3)+1] = (char)(235-i); // green
    pal[(i*3)+2] = 0;           // blue
    }

// and fade red down
for(i=236;i!=255;i++)
    {
    pal[(i*3)]   = (char)(299-i); // red
    pal[(i*3)+1] = 0; // green
    pal[(i*3)+2] = 0; // blue
    }
//WHITE 255
    pal[(255*3)+0] = 63;
    pal[(255*3)+1] = 63;
    pal[(255*3)+2] = 63;
```

```
asm     {
        mov     ax,ds
        mov     es,ax
        mov     ax,1012h
        mov     bx,0000h
        mov     cx,256
        mov     dx,offset pal
        int     10h
        }
} // end of setpalette //*******************************************************************
// Function plots the provided display data acording to the provided
// screen draw lookup table.
// The data is a list of values to be plotted.  The length is variable,
// termineated by 0.
// For every data point, the lookup table describes a region to fill
// with that value (color).  The lookup table consists of pairs of integers:
//              Starting address
//              Ending address
//              Starting address
//              Ending address
//              NULL
//              Starting address
//                :         :
// A null starting address indicates that that region is complete.

void PlotCSA(char* viddata,unsigned int* lookup)
{
int i,j;
register unsigned int index,endindex;
register char far *s;

s = (char*)MK_FP(0xa000,0);
i = 0; // data table pointer
j = 0; // lookup table pointer
while(lookup[j]) // check for terminating NULL
    {
    while(lookup[j]) // check for non-null starting value
        {
        index = lookup[j++];
        endindex = lookup[j++];
        while(index++ != endindex && index < 64000)
            {
            s[index] = viddata[i]; // write pixels out
            }
        }
    i++; // moving to next region
    j++; // get past the null
    }
} // end of PlotCSA
```

```c
/*
* Serial driver for conductivity analyser
* File SER.CPP
* This driver makes no attempt to be generic, but is a highly optimized
* serial driver for the conductivity analyzer.
* Recieved messages are interrupt driven, and the interrupt routine stores
* the data directly in the appropriate place.
* last revised 3/28/93
*/ include <stdio.h>
include <conio.h>
include <dos.h> define  com1_data   0x3f8 // transmit and recieve data in/out
define  com1_ier    0x3f9 // Interrupt enable register
    /*----------------------------------------------------------------*
        Bit values held in the Interrupt Enable Register (IER).
        bit     meaning
        ---     -------
        0       Interrupt when data received.
        1       Interrupt when transmitter holding reg. empty.
        2       Interrupt when data reception error.
        3       Interrupt when change in modem status register.
        4-7     Not used.
    *----------------------------------------------------------------*/ define  com1_iir    0x3fa // Interrupt id
    /*----------------------------------------------------------------*
        Bit values held in the Interrupt Identification Register (IIR).
        bit     meaning
        ---     -------
        0       Interrupt pending
        1-2             Interrupt ID code
           00=Change in modem status register,
           01=Transmitter holding register empty,
           10=Data received,
           11=reception error, or break encountered.
        3-7     Not used.
    *----------------------------------------------------------------*/ define  com1_lcr    0x3fb // Line control register
    /*----------------------------------------------------------------*
        Bit values held in the Line Control Register (LCR).
        bit     meaning
        ---     -------
        0-1      00=5 bits, 01=6 bits, 10=7 bits, 11=8 bits.
        2       Stop bits.
        3       0=parity off, 1=parity on.
        4       0=parity odd, 1=parity even.
        5       Sticky parity.
        6       Set break.
        7       Toggle port addresses.
    *----------------------------------------------------------------*/
#define  com1_mcr    0x3fc // Modem control register
    /*----------------------------------------------------------------*
        Bit values held in the Modem Output Control Register (MCR).
        bit     meaning
        ---     -------
        0       Data Terminal Ready. Computer ready to go.
```

```
    1       Request To Send. Computer wants to send data.
    2       auxillary output #1.
    3       auxillary output #2.(Note: This bit must be
            set to allow the communications card to send
            interrupts to the system)
    4       UART output looped back as input.
    5-7     not used.
*---------------------------------------------------------------------*/ define  com1_lsr   0x3fd  // Line status register
/*---------------------------------------------------------------------*
    Bit values held in the Line Status Register (LSR).
    bit     meaning
    ---     -------
    0       Data ready.
    1       Overrun error - Data register overwritten.
    2       Parity error - bad transmission.
    3       Framing error - No stop bit was found.
    4       Break detect - End to transmission requested.
    5       Transmitter holding register is empty.
    6       Transmitter shift register is empty.
    7              Time out - off line.
*---------------------------------------------------------------------*/
#define  com1_msr   0x3fe  // Modem status register
/*---------------------------------------------------------------------*
    Bit values held in the Modem Input Status Register (MSR).
    bit     meaning
    ---     -------
    0       delta Clear To Send.
    1       delta Data Set Ready.
    2       delta Ring Indicator.
    3       delta Data Carrier Detect.
    4       Clear To Send.
    5       Data Set Ready.
    6       Ring Indicator.
    7       Data Carrier Detect.
*---------------------------------------------------------------------*/ define  com1_dll   0x3f8  // Baud rate divisor latch low when DLAB active
define  com1_dlh   0x3f9  // Baud rate divisor latch high when DLAB is active /*
    These are the port addresses of the 8259 Programmable Interrupt
    Controller (PIC).
*/
#define IMR          0x21    /* Interrupt Mask Register port */
#define ICR          0x20    /* Interrupt Control Port       */

/*
    An end of interrupt needs to be sent to the Control Port of
    the 8259 when a hardware interrupt ends.
*/
#define EOI          0x20    /* End Of Interrupt */

/*
    The (IMR) tells the (PIC) to service an interrupt only if it
    is not masked (FALSE).
*/
#define IRQ3         0xF7    /* COM2 */
```

```c
define IRQ4          0xEF   /* COM1 */ static int oldCOM1irqSeg; // this stores the old COM1 interrupt vector
static int oldCOM1irqOff;

#define RX_CIR_BUF  100
static char circular[RX_CIR_BUF];   // circular buffer
int    head = 0;      // head pointer
int    tail = 0;      // tail pointer
int    overrun = 0;   // buffer overrun flag int    RTdata[500];   // runtime data storage location
int    NumRTdata = 0;// number of runtime data points (pairs of recieved bytes)
int    RTstate = -1;  // used by the run time IRQ to control the reading //*****************************************************************************
// RS232 buffered interrupt procedure static void interrupt SerialBIRQ(void)
{ circular[head] = inportb(com1_data);
head++; // increment buffer pointer
if(head == tail)     // check for overrun
   {overrun = 1;} if(head == RX_CIR_BUF) // buffer wrap
   {head = 0;} asm   {
      sti              // turn interrupts back on
      mov   al,EOI     // send EndOfInt to 8259
      out   ICR,al     // send to interrupt control port
      }
} // end of SerialBIRQ //*****************************************************************************
// Serial buffer read procedure
// if read is attempted when empty, returns the previous char char GetCirBuf(void)
{
char c;
disable();           // disables interrupts
c = circular[tail];

if(tail != head)     // check for empty buffer
   {tail++;} if(tail == RX_CIR_BUF) // buffer wrap
   {tail = 0;}
return(c);
} // end of GetCirBuf //*****************************************************************************
// Test Serial buffer empty
// returns 0 if empty
```

```c
int CirBufNotEmpty(void)
{
return(head-tail);
} // end of CirBufNotEmpty

//*********************************************************************
// RS232 run time interrupt procedure
// When in state -1: waiting for a NULL to be recieved
// Once recieved, will buffer first byte, then add to second byte and
// store the data point in the RTdata array.
// static void interrupt SerialRTIRQ(void)
{
static char OneBuff;
static char ByteSaved; // flag indicating that OneBuff is loaded if(RTstate == -1) // check if state = -1 i.e. waiting for null
   {
   if(!inportb(com1_data)) // check for NULL recieved
      {
      RTstate = 0;
      ByteSaved = 0;
      }
   }
else
   { // get char and process
   if(ByteSaved) // check if byte in buffer
      { // byte already in buffer
      (_AL) = inportb(com1_data); // get LSB in AL register
      asm   { // assembly used to merge the MSB and LSB
            mov AH,OneBuff    // put 7 bit MSB in AH register
            shl AL,1          // make bit 6(in AL) next to bit 7 (in AH)
            shr AX,1          // now a 14 bit number in AX
            }
      RTdata[RTstate] = (_AX); // save 14 bit result in data array
      RTstate++; // update data pointer
      if(RTstate == NumRTdata)   // if
         {RTstate = -1;}
      ByteSaved = 0; // clear saved flag
      }
   else
      { // no byte in buffer ; save MSB there
      OneBuff = inportb(com1_data);
      ByteSaved++; // remember byte saved
      }
   } asm   {
      sti               // turn interrupts back on
      mov   al,EOI      // send EndOfInt to 8259
      out   ICR,al      // send to interrupt control port
      }
} // end of SerialRTIRQ //*********************************************************************
// Get data table
// provided to make easy access for routines in CONDUCT.CPP
```

```
int GetDataTable(int TabPtr)
{
return(RTdata[TabPtr]);
} // end of GetDataTable //*********************************************************************
/* This loads a general purpose reciever that puts messages into a
 * circular buffer.
 */ void OpenSerialBuffered(void)
{
int portdata;   // one word used to transfer data to/from port addresses
// first set interrupt vector to my routine
asm     {

// save the current interrupt vector
        mov     ah,35h      // this is DOS function 35 int21 : Get Interrupt Vector
        mov     al,0Ch      // this is the COM1 interrupt number
        int     21h         // segment in es, offset in bx
        mov     oldCOM1irqOff,bx
        mov     bx,es
        mov     oldCOM1irqSeg,bx // next set the vector to the new serial interrupt routine
        push    ds
        mov     ah,25h      // this is DOS function 25 int21 : Set Interrupt Vector
        mov     al,0Ch      // this is the COM1 interrupt number
        mov     dx,offset SerialBIRQ
        mov     bx,seg SerialBIRQ
        mov     ds,bx
        int     21h
        pop     ds
        }
disable();
// first configure COM1 for interrupt on recieve char only
outportb(com1_ier,0x0001);

// now set modem control to "interrupt on"
outportb(com1_mcr,0x000b);

// now unmask IRQ4 for COM1
portdata = inportb(IMR);  // get interrupt mask register
portdata = portdata & IRQ4;   // turn on COM1 interrrupt
outportb(IMR,portdata);
enable();
} // end of OpenSerial //*********************************************************************
/* This loads a high speed message handler that automatically sorts the
 * recieved data into the appropriate locations.
 */ void OpenSerialRunTime(int NumDataPoints)
{
int portdata;   // one word used to transfer data to/from port addresses // first set number of data points to be read by IRQ
NumRTdata = NumDataPoints;
```

```
// next set interrupt vector to my routine
asm    {

// save the current interrupt vector
       mov    ah,35h   // this is DOS function 35 int21 : Get Interrupt Vector
       mov    al,0Ch   // this is the COM1 interrupt number
       int    21h      // segment in es, offset in bx
       mov    oldCOM1irqOff,bx
       mov    bx,es
       mov    oldCOM1irqSeg,bx // next set the vector to the new serial interrupt routine
       push   ds
       mov    ah,25h   // this is DOS function 25 int21 : Set Interrupt Vector
       mov    al,0Ch   // this is the COM1 interrupt number
       mov    dx,offset SerialRTIRQ
       mov    bx,seg SerialRTIRQ
       mov    ds,bx
       int    21h
       pop    ds
       }
disable();
// first configure COM1 for interrupt on recieve char only
outportb(com1_ier,0x0001);

// now set modem control to "interrupt on"
outportb(com1_mcr,0x000b);

// now unmask IRQ4 for COM1
portdata = inportb(IMR); // get interrupt mask register
portdata = portdata & IRQ4;    // turn on COM1 interrrupt
outportb(IMR,portdata);
enable();
} // end of OpenSerial

//******************************************************************** void CloseSerial(void)
{
int portdata;
asm    {
       // restore the original interrupt vector
       push   ds
       mov    ah,25h   // this is DOS function 25 int21 : Set Interrupt Vector
       mov    al,0Ch   // this is the COM1 interrupt number
       mov    dx,oldCOM1irqOff
       mov    bx,oldCOM1irqSeg
       mov    ds,bx
       int    21h
       pop    ds
       }
// mask IRQ4 for COM1
disable();
portdata = inportb(IMR); // get interrupt mask register
portdata = portdata | -IRQ4;   // turn off COM1 interrrupt
outportb(IMR,portdata);

// now set modem control to "interrupt off"
outportb(com1_mcr,0x0000);
```

```c
// clear COM1 interrupt configuration
outportb(com1_ier,0x0000);
enable();
} // end of CloseSerial //*******************************************************************
int SetupCOM1()
{
/* note: a buad rate was required that could be implemented on the PC
         and on the 80C32.  The optimal rate seems to be 38,400 baud
         which can be obtained on the PC and on the 80C451 with a 14.7456Mhz
         crystal.  The opto isolator can handle this rate satisfactorily
*/

//#define Speed 1200
#define Speed 38400
int portdata;  // one word used to transfer data to/from port addresses
int divisor;   // used to hold baud rate divisor
int Returnval = 0;

// This routine sets the baud rate, parity, #data bits and #stop bits

// First set the baud rate
// Setting the speed requires that the DLAB be set on.
divisor = (int) (115200L/Speed);
disable();   // disable interrupts
portdata = inportb(com1_lcr);   // read line status register
outportb(com1_lcr, (portdata | 0x80)); // Set DLAB so baud rate can be written
outportb(com1_dll, (divisor & 0x00FF));
outportb(com1_dlh, ((divisor >> 8) & 0x00FF));
outportb(com1_lcr, portdata);          // Reset DLAB // now set parity,data bits and stop bits outportb(com1_lcr,0x001a); // 7 data, even, 1 stop
outportb(com1_lsr,0x0060); // clear the line status register enable();   // reenable interrupts return (Returnval);
}

//*******************************************************************
void outCOM1(char sendchar)
{
//first verify that holding register is empty
while( !(0x20 & inportb(com1_lsr)))
   {;} // wait for transmitter free
outportb(com1_data,sendchar);
}
//*******************************************************************
void stringCOM1(char send[])
{
int i = 0;
char c;
while( c=send[i++]) // check for NULL
   {outCOM1(c);}   // send
}
```

```
//*********************************************************************
// 0 is no error
// 2 is Overrun error
// 4 is Parity error
// 8 is Framing error int CommError()
{
return((char)(0x0E & inportb(com1_lsr)));
} // end of CommError

//********************************************************************* void ClearCirBuf(void)
{
disable();
head = 0;
tail = 0;
enable();
} // end of ClearCirBuf

//*********************************************************************
```

What is claimed is:

1. A concentration analyzer for determining the cross-sectional concentration at multiple locations within the cross section of a moving fluid stream of dissolved substances within said moving fluid flow stream consisting of a first solution of unknown concentration, comprising:

injection means, for introducing a second solution of known concentration of dissolved substances into the fluid flow;

sensor means, for measuring the conductivity of the first solution and second solution mixture wherein the sensor means comprises a plurality of electrodes configured with a center probe electrode and two outer hexagonal rings of electrodes for transmitting signals relating to sensed conductivity;

a constant current source, connected to a pair of said electrodes at any one time interval, for applying current to said pair of said electrodes;

a conductance meter which receives the transmitted signals from said electrodes and converts the signals to conductivity measurements; and an interface connector, comprising a plurality of pins connected to said plurality of electrodes and to said conductance meter;

storage means, for storing the measured conductivity at a plurality of time intervals as the moving fluid stream continues moving; and computing means, for converting the measured conductivity into a concentration value and for computing the concentration of the first solution based upon the known concentration of the second solution.

2. A concentration analyzer for determining the cross-sectional concentration at multiple locations within the cross section of a moving fluid stream of dissolved substances within said moving fluid flow stream consisting of a first solution of unknown concentration, comprising:

injection means, for introducing a second solution of known concentration of dissolved substances into the fluid flow;

sensor means, for measuring the conductivity of the first solution and second solution mixture wherein the sensor means comprises a plurality of electrodes configured with a center probe electrode and two outer hexagonal rings of electrodes for transmitting signals relating to sensed conductivity;

a constant current source, connected to a pair of said electrodes at any one time interval, for applying current to said pair of said electrodes;

a conductance meter which receives the transmitted signals from said electrodes and converts the signals to conductivity measurements, wherein said conductance meter comprises an input multiplexer comprising a plurality of channels, the number of said plurality of channels being equal to the number of said plurality of electrodes;

an instrumentation amplifier;

wherein any two of said plurality of channels can be activated at a predetermined time by connecting one of said channels at one end to said constant current source and by connecting another of said channels at one end to ground, thereby activating two of said channels, and by connecting the other end of each of said two activated channels to said instrumentation amplifier, said instrumentation amplifier amplifying the differential potential between said two activated channels;

an interface connector, comprising a plurality of pins connected to said plurality of electrodes and to said conductance meter; storage means, for storing the measured conductivity at a plurality of time intervals as the moving fluid stream continues moving; and computing means, for converting the measured conductivity into a concentration value and for computing the concentration of the first solution based upon the known concentration of the second solution.

3. A concentration analyzer for determining the cross-sectional concentration at multiple locations within the cross section of a moving fluid stream of dissolved substances within said moving fluid flow stream consisting of a first solution of unknown concentration, comprising:

injection means, for introducing a second solution of known concentration of dissolved substances into the fluid flow;

sensor means, for measuring the conductivity of the first solution and second solution mixture wherein the sensor means comprises a plurality of electrodes configured with a center probe electrode and two outer hexagonal rings of electrodes for transmitting signals relating to sensed conductivity;

a constant current source, connected to a pair of said electrodes at any one time interval, for applying current to said pair of said electrodes, wherein said constant current source comprises a constant mirror comparator for generating said constant current;

a conductance meter which receives the transmitted signals from said electrodes and converts the signals to conductivity measurements; and an interface connector, comprising a plurality of pins connected to said plurality of electrodes and to said conductance meter;

storage means, for storing the measured conductivity at a plurality of time intervals as the moving fluid stream continues moving; and computing means, for converting the measured conductivity into a concentration value and for computing the concentration of the first solution based upon the known concentration of the second solution.

* * * * *